(12) United States Patent
Hearing et al.

(10) Patent No.: US 7,585,498 B2
(45) Date of Patent: Sep. 8, 2009

(54) REGULATION OF ADENOVIRUS DNA PACKAGING BY IPTG

(75) Inventors: Patrick Hearing, St. James, NY (US); Amy Ostrom, Lake Worth, FL (US); Susanne Wells, Cincinnati, OH (US)

(73) Assignee: The Research Foundation of State University of New York, Albany, NY (US)

( * ) Notice: Subject to any disclaimer, the term of this patent is extended or adjusted under 35 U.S.C. 154(b) by 220 days.

(21) Appl. No.: 10/490,551

(22) PCT Filed: Sep. 25, 2002

(86) PCT No.: PCT/US02/30318

§ 371 (c)(1),
(2), (4) Date: Feb. 1, 2005

(87) PCT Pub. No.: WO03/027271

PCT Pub. Date: Apr. 3, 2003

(65) Prior Publication Data

US 2006/0073595 A1   Apr. 6, 2006

Related U.S. Application Data

(60) Provisional application No. 60/324,838, filed on Sep. 25, 2001.

(51) Int. Cl.
| | |
|---|---|
| *C12N 15/00* | (2006.01) |
| *C12N 15/72* | (2006.01) |
| *C12N 15/86* | (2006.01) |
| *C12N 15/861* | (2006.01) |
| *C12N 15/63* | (2006.01) |
| *C12N 15/64* | (2006.01) |
| *C12N 5/06* | (2006.01) |

(52) U.S. Cl. .................. 424/93.2; 424/93.21; 435/69.1; 435/320.1; 435/455; 435/456; 435/457; 536/24.1

(58) Field of Classification Search ....................... None
See application file for complete search history.

(56) References Cited

U.S. PATENT DOCUMENTS 5,674,730 A * 10/1997 Baim et al. ................. 435/353

FOREIGN PATENT DOCUMENTS

WO    WO 99/53085    10/1999

OTHER PUBLICATIONS

Fuerst et al, Transfer of the inducible lac repressor/operator system from *Escherichia coli* to a vaccinia virus expression vector, Proc. Nati. Acad. Sci. USA vol. 86, pp. 2549-2553, Apr. 1989.*
Ostrom, Amy, Studies of Adenovirus Type 5 DNA Packaging and Development of a Novel Adenovirus Helper Virus, 2001, Dissertation, State University of New York, Stony Brook, NY part 1-5.*
Barjot et al. (2002) "Gutted adenoviral vector growth using E1/E2b/E3-deleted helper viruses" *The Journal of Gene Medicine*, 4:480-489.
Matthews et al. (1999) "Development and use of a 293 cell line expressing lac repressor for the rescue of recombinant adenoviruses expressing high levels of rabies virus glycoprotein", *Journal of General Virology*, 80:345-353.

* cited by examiner

*Primary Examiner*—Maria Marvich
(74) *Attorney, Agent, or Firm*—Meldon & Carroll, LLP

(57) ABSTRACT

The present invention relates to recombinant Adenoviruses (Ad) which function as helper viruses to gutted Ad viruses lacking viral coding sequences. The recombinant Ad of the present invention comprise a binding site of the *E. coli* Lac repressor protein embedded within the packaging domain. Available Lac repressor protein binds to its operator site within the helper virus packaging domain, precluding the binding of natural packaging factors. The present invention also provides recombinant Ad which in addition to having a binding site for the Lac repressor protein within the packaging domain, also comprise coding sequence for the Lac repressor protein under the control of a promoter which functions in producer cells. Methods for suppressing packaging of helper Ad during packaging of a gutted Ad vector are also provided as are methods of producing recombinant helper Ad using lactose or lactose derivative as a regulatory molecule. Temperature shift may also be used to regulate growth of a recombinant helper Ad. In addition, methods of producing a gutted Ad vector substantially free of helper Ad are provided.

21 Claims, 15 Drawing Sheets

REGULATION OF ADENOVIRUS DNA PACKAGING BY IPTG

CROSS REFERENCE TO RELATED APPLICATIONS

This application is a section 371 application of PCT International application No. PCT/US02/30318, having an International Filing Date of Sep. 25, 2002, which claims priority to U.S. Provisional Application No. 60/324,838, filed Sep. 25, 2001, the contents of which are incorporated by reference.

This invention described herein was made in part under NIH Grant AI41636. The United States government may have certain rights in the invention.

BACKGROUND OF THE INVENTION

Recombinant Adenoviruses (Ad) show great promise as vectors for the treatment of disease by gene therapy. Somatic gene therapy is defined as the treatment of inherited or acquired diseases by the introduction and expression of genetic information in somatic cells. Candidate disorders for somatic gene therapy include inherited metabolic disorders as well as acquired diseases including several types of cancer. Because of their intrinsic ability to enter cells carrying along their own genetic material, viruses are widely used as gene delivery vectors for living organisms. Advantages of employing Ad as a gene therapy vector are many: the genetic organization and functions of many gene products have been characterized, the virus infects a wide host cell range, the virus is capable of productive infection of resting cells, the genome is easily manipulated, and recombinant viruses can be grown to high titer in the laboratory. Finally, Ad infection is relatively benign and has not been associated with any human malignancy. It has been shown in animal studies and human clinical trials however, that Ad invokes an inflammatory response soon after infection, followed by a cytotoxic T cell response directed against virus-infected cells. Innate host defenses, such as recruitment of macrophages and activation of complement and natural killer cells, are thought to play a substantial role in the clearance of an Ad infection iii vivo (Worgall, Leopold et al. 1997; Worgall, Singh et al. 1999). This clearance of virus-infected cells ultimately leads to cessation of foreign gene expression. A number of classes of Ad vectors exist, each eliciting the immune response to varying degrees.

Viruses rendered replication-defective by the deletion of one or more early genes have demonstrated their potential usefulness in animal models of cancer for example (Addison, Braciak et al. 1995; Addison, Gauldie et al. 1995). In such first generation vectors, the E1 and/or E3 gene cassettes are removed, allowing the introduction of up to 6.5 kb of transgene (Graham, Smiley et al. 1977) under the control of a heterologous promoter. Removal of the E1 region results in impaired transcription of the E2 genes and, consequently, an impairment of viral DNA replication and production of viral proteins, and thereby reduces the host immune response to viral proteins. The defective E1 viruses are propagated in an E1-complementing cell line, such as 293 cells, that provide the E1 gene products in trans. Although some first generation Ad vectors have shown promise for certain applications, such as cancer therapy, the expression of the transgene in vivo has been shown to be transient, and an overwhelming immune response is mounted by the host. Deletion of the E3 coding region allows for larger transgene inserts, but further renders the cells susceptible to apoptosis, as a result of the elimination of the E3 gene-mediated defenses against host responses (Poller, Schneider-Rasp et al. 1996).

Second and third generation vectors lack the E2 genes, in addition to the E1 and E3 genes (Lusky, Christ et al. 1998; O'Neal, Zhou et al. 1998). Even with the E2 deletions, however, the host immune response is still a daunting impediment to achieving persistent transgene expression. The generation of replication-competent Ad (RCA) through recombination between Ad sequences within the cell line and the recombinant vector has prevented the production of pure stocks of all of the early generation vectors.

Improvements made on early generation vectors have culminated in the development of helper-dependent (HD) or gutted vectors deleted of most or all Ad coding sequences. Gutted vectors allow for nearly 36 kb of transgene sequences as well as a reduced host immune response (Kochanek, Clemens et al. 1996; Parks, Chen et al. 1996). These vectors show great potential as gene transfer vectors for gene therapy as long-term expression of therapeutic genes has been observed in mice and monkeys (Chen, Mack et al. 1997; Morral, Parks et al. 1998; Morsy, Gu et al. 1998; Schiedner, Morral et al. 1998; Morral, O'Neal et al. 1999). The production of such vectors in tissue culture relies upon a complementing helper virus to provide the proteins in trans that are required for growth and assembly of the gutted vector. A significant barrier to wider application of gutted vectors, however, is the production of pure gutted vector stocks. Although the gutted vector lacks virtually all Ad sequences, except those cis-acting elements required for DNA replication and packaging, the use of these vectors has been limited by high levels of contaminating helper virus. Contamination with high levels of helper virus is unacceptable in a gene therapy application. One approach to limit contamination with helper virus is to alter the packaging sequences of the two vectors to eliminate sequence overlap (Sandig, Youil et al. 2000). A second approach to limit contamination with helper virus is biological selection based on Cre recombinase-mediated excision of the helper genome's packaging signal via loxP sites during gutted vector production (Parks, Chen et al. 1996; Hardy, Kitamura et al. 1997). In this Cre-lox system, the helper virus contains two loxP recognition sequences flanking the packaging domain. To produce the gutted vector, cells that express the Cre-recombinase of bacteriophage P1 are coinfected with the helper virus and gutted vector. In these production cells, the packaging domain of the helper virus is excised with high efficiency so that packaging of the helper virus is greatly reduced and the majority of packaged genomes are gutted virus genomes. This method of production reduces the contamination of gutted vector with helper virus to $\leq 1\%$ after purification of virus particles by CsCl centrifugation. Although this system has resulted in higher titers of gutted vector preparations with low helper virus contamination compared to other systems, the Cre-mediated excision is not 100% effective and all groups report some level of contamination.

The Ad5 packaging domain consists of at least seven cis-acting sequences termed A repeats I-VII. It is thought that these cis-acting sequences are binding sites for an unidentified trans-acting protein(s), and that this interaction is required to mediate DNA packaging. In accordance with the present invention, binding sites for the *E. coli* Lac repressor protein have been inserted within the packaging domain of the helper virus and between the critical A repeats. One domain of the repressor protein binds to an operator sequence that shares some homology with the Ad packaging domain, while another domain binds the inducer isopropyl-β-D-thiogalactopyranoside (IPTG). In place of the Ad E1 genes, a CMV promoter-driven lacI expression cassette has been inserted. In the presence of IPTG, the virally expressed Lac repressor is not bound to the packaging domain and DNA packaging of the helper virus genome ensues. In the absence of IPTG, however, Lac repressor protein binds to its sites embedded within the packaging domain of the helper virus genome. This binding by Lac repressor protein precludes the natural packaging factor(s) from binding and therefore DNA packaging of the helper virus genome is suppressed. The subject Ad helper virus is capable of specifically suppressing its own DNA packaging while providing all of the proteins required in trans to replicate and package a gutted Ad genome. This method of regulation, used alone or in combination with the Cre-lox system, results in a helper Ad capable of generating high-titer gutted Ad vector stocks substantially free of helper virus contamination.

SUMMARY OF THE INVENTION

The present invention provides a recombinant helper Adenovirus (Ad) comprising: trans-acting Ad sequences required for growth and assembly of a gutted Ad, and at least one binding site for Lac repressor located within the packaging domain of the recombinant helper Ad, wherein binding of the Lac repressor to the binding site and packaging of the recombinant helper Ad is regulatable in a producer cell by temperature shift or administration of lactose or lactose derivative. Preferably, the binding site for the Lac repressor is located within critical cis-acting packaging A repeats.

The recombinant helper Ad of the present invention may further comprise coding sequence for the Lac repressor operably linked to a promoter which functions in the producer cell. In one embodiment, coding sequence for the Lac repressor is a temperature sensitive mutant coding sequence. Producer cells and lysate stock comprising a subject recombinant helper Ad are also provided.

The present invention also provides a method for producing a gutted Ad substantially free of contaminating helper Ad. The method comprises the steps of: (a) cotransfecting a producer cell(s) with (i) a gutted Ad vector, (ii) a recombinant helper Ad comprising trans-acting Ad sequences required for growth and assembly of a gutted Ad vector and at least one binding site for Lac repressor located within the packaging domain of the recombinant helper Ad, and (iii) a vector comprising coding sequence for Lac repressor protein operatively linked to a promoter which functions in the producer cell(s);

(b) growing the producer cells for a suitable time under conditions favorable for growth and packaging of the gutted Ad; and (c) suppressing packaging of the recombinant helper Ad by expression of the Lac repressor in the producer cells.

Alternatively, a method for producing a gutted Ad substantially free of contaminating helper Ad comprises the steps of: (a) cotransfecting a producer cell(s) with: (i) a gutted Ad vector, (ii) a recombinant helper Ad comprising trans-acting Ad sequences required for growth and assembly of a gutted Ad vector and at least one binding site for Lac repressor located within the packaging domain of the recombinant helper Ad, wherein the recombinant helper Ad also comprises coding sequence for the Lac repressor operably linked to a promoter which functions in the producer cells;

(b) growing the producer cells for a suitable time under conditions favorable for growth and packaging of the gutted Ad; and (c) suppressing packaging of the recombinant helper Ad by expression of the Lac repressor in the producer cells.

The gutted Ad produced by the methods of the invention may further comprise a nucleotide sequence for a heterologous protein. Preferably, the heterologous protein is a therapeutic protein useful for the treatment of disease by gene therapy.

In another embodiment, there is provided a method for producing a gutted Ad substantially free of helper Ad, said method comprising: (a) cotransfecting a producer cell(s) with (i) a gutted Ad vector, (ii) a recombinant helper Ad comprising trans-acting Ad sequences required for growth and assembly of a gutted Ad vector and at least one binding site for Lac repressor located within the packaging domain of the recombinant helper Ad, wherein the producer cell(s) is capable of endogenous expression of the Lac repressor;

(b) growing the producer cells for a suitable time under conditions favorable for growth and packaging of the gutted Ad while suppressing packaging of the recombinant helper Ad by expression of the Lac repressor in the producer cell(s).

In another aspect of the invention, there are provided methods for producing a subject recombinant helper Ad. In one embodiment, the method comprises the steps of transfecting a producer cell(s) with a subject Ad, and growing the producer cells for a suitable time in the presence of lactose or a lactose derivative. In another embodiment, the method comprises the steps of transfecting a producer cell(s) with a subject Ad comprising coding sequence for a temperature sensitive Lac repressor, and growing the producer cells for a suitable time at a restrictive temperature for the Lac repressor. A recombinant helper Ad of the present invention may be produced in the same or a different producer cell(s) than a gutted Ad vector.

Packaging of a subject recombinant helper Ad may be regulated by lactose or a lactose derivative. Examples of lactose derivatives include but are not limited to methyl 1-thio-β-D-galactoside, n-propyl 1-thio-β-D-galactoside, n-butyl β-D-galactoside, n-butyl 1-thio-β-D-galactoside, allolactose (6-O-β-galactopyranosyl-D-glucose), thio-allolactose (6(S)-galactopyranosyl-D-glucose), and isopropyl-β-D-thiogalactopyranoside (IPTG). Preferably, IPTG is used to regulate packaging.

Figure 1:
FIG. 1 is a schematic of a gutted Ad gene therapy vector (top) and an Ad helper virus (bottom) that provides complementation in trans for production of the gutted virus.
Figure 1:
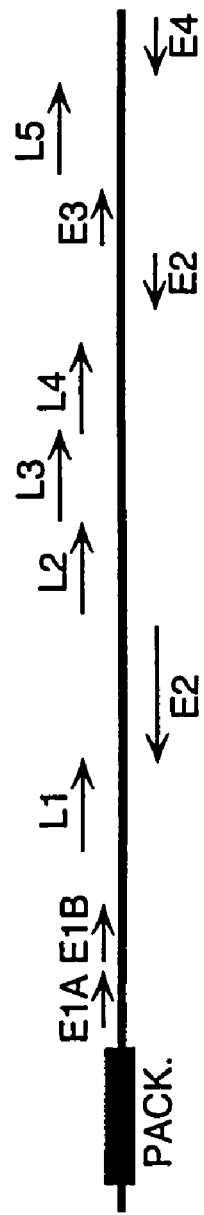

The radiolabeled lac binding site monomer probe was incubated with mock WCE in lanes 1 and 2, in the presence of monoclonal antibody M45 in lane 2. The probe was incubated with LacWT WCE in lanes 3 and 4, in the presence of monoclonal M45 antibody in lane 4. The probe was incubated with LacX86 WCE in lanes 5 and 6, in the presence of monoclonal antibody M45 in lane 6. The arrows to the left of the gel denote the specific binding activities and supershifted complexes on the lac binding site probe (upper arrows) and the position of free DNA probe (lower arrows).

Figure 5:
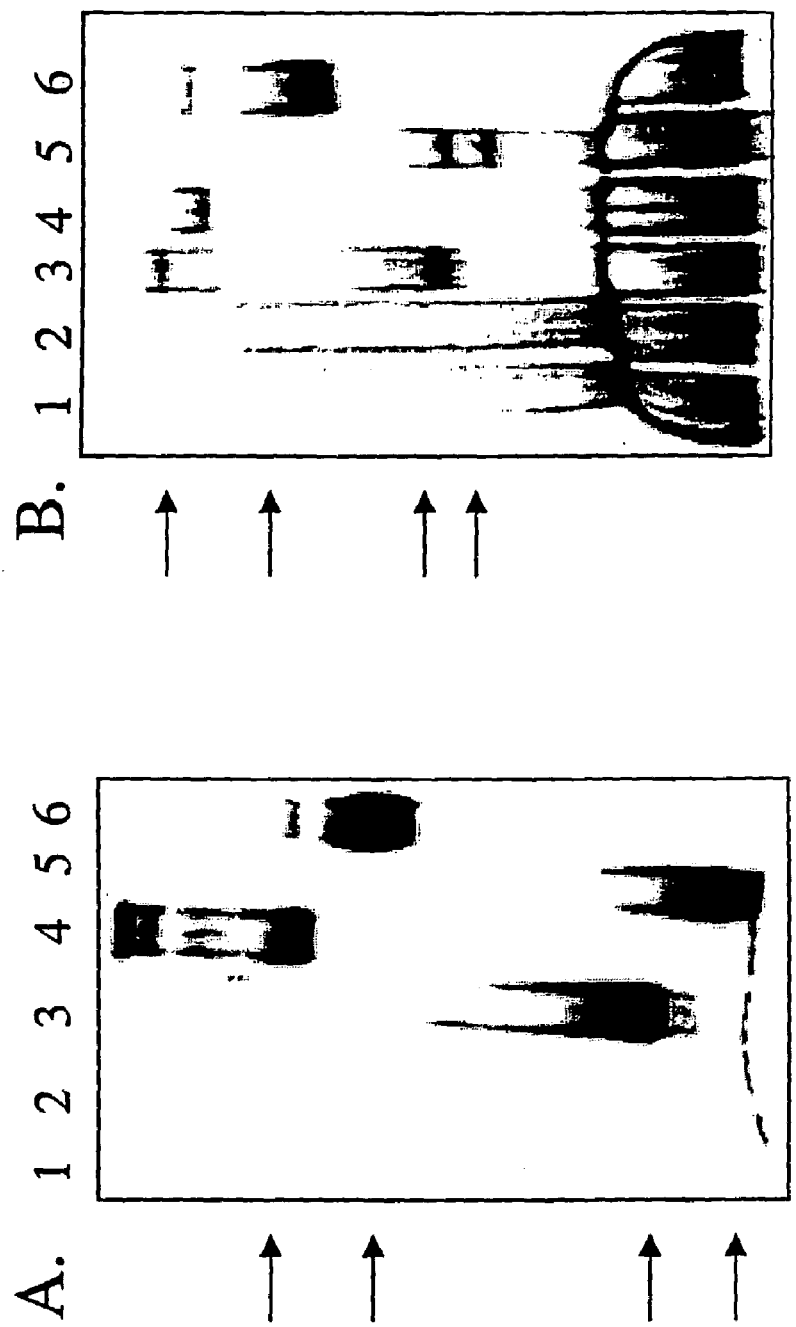
FIG. 5A shows in vitro gel mobility shift assays of M45 epitope-tagged Lac repressor protein prepared from whole cell extracts (WCE). A gel shift experiment was performed using extract prepared from 293 cells transfected with the pCMX-M45-LacWT and pCMX-M45-LacX86 plasmids.

FIG. 5B shows a gel mobility shift experiment using the extracts described for FIG. 5A and a radiolabeled AV-VII(lac)$^2$ dimer probe. The order of the lanes is of that described in A. The arrows to the left of the gel denote the Lac repressor-specific binding activities (lower arrows) and antibody supershifted complexes (upper arrows) on the AV-VII(lac)$^2$ dimer probe. The nature of the two upper bands in lanes 3 and 5 is unknown, but they may represent binding to both lac sites on the dimer probe. Free DNA probe is seen at the bottom of the gel.

Figure 6:
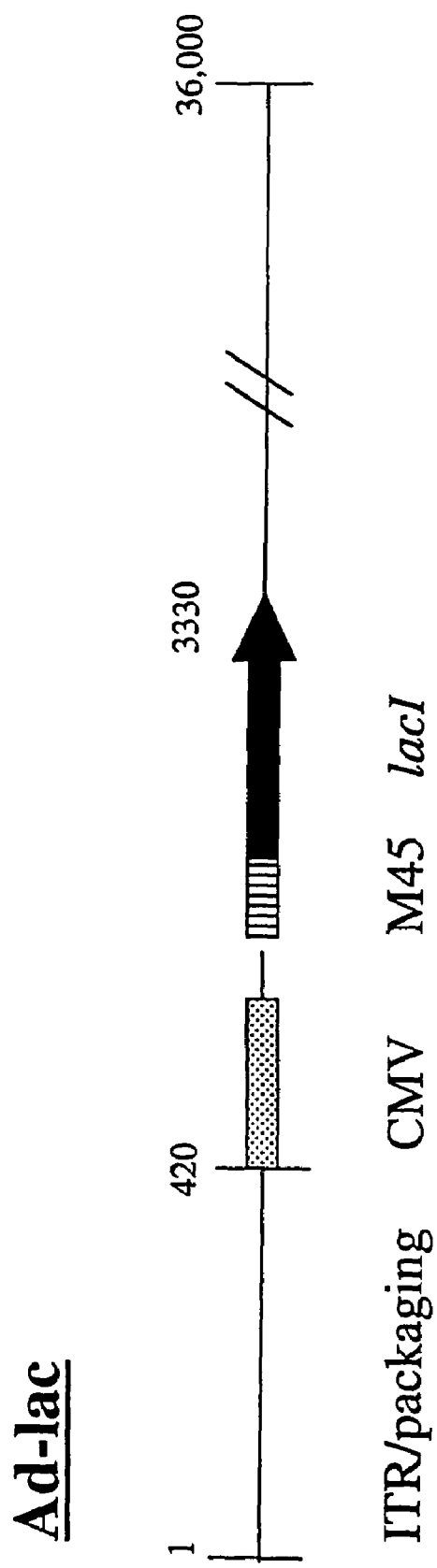

FIG. 6 is a schematic of Ad-LacWT. The ITR/packaging domain is shown at the left end. The CMV-M45-Lac repressor cassette is denoted by rectangles in place of Ad nucleotides 420 and 3330.

Figure 7:
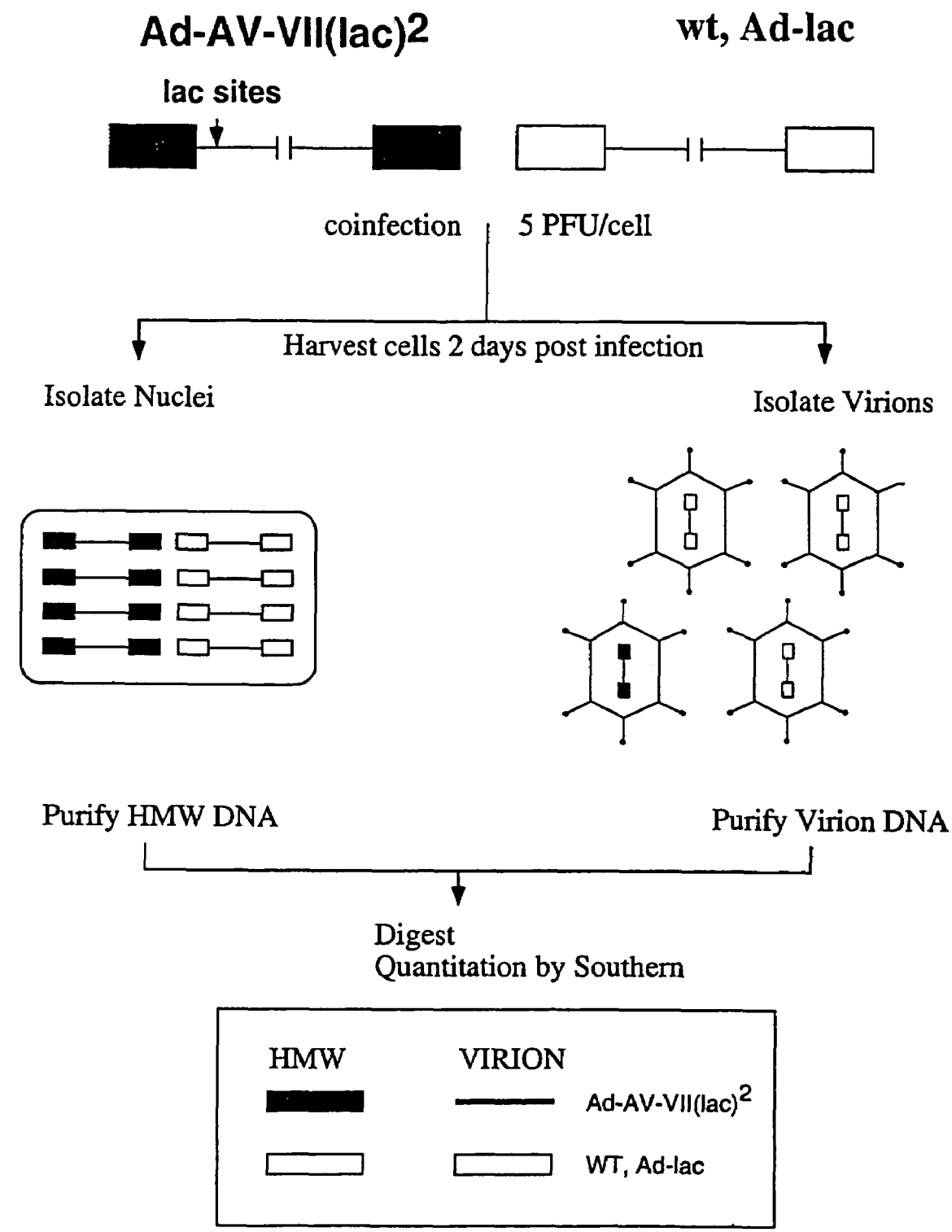

FIG. 7 is a schematic depicting the analysis of coinfection experiments by restriction enzyme digestion and Southern blotting. The packaging efficiency of Ad-AV-VII(lac)$^2$ virus was determined in an infection of 293 cells with a coinfecting virus (e.g., Ad-LacWT). 48 hr post-infection, a portion of the cells was used to isolate total nuclear DNA and the remaining portion was used for the preparation of viral DNA from purified virus particles. Both DNA preparations were digested with diagnostic restriction enzymes to distinguish between input viral DNAs and analyzed by Southern blot hybridization using an Ad left-end fragment as probe. Quantitation of virus-specific bands in the Southern blot was performed using a Molecular Dynamics Storm 860 phosphoimager.

Figure 8:
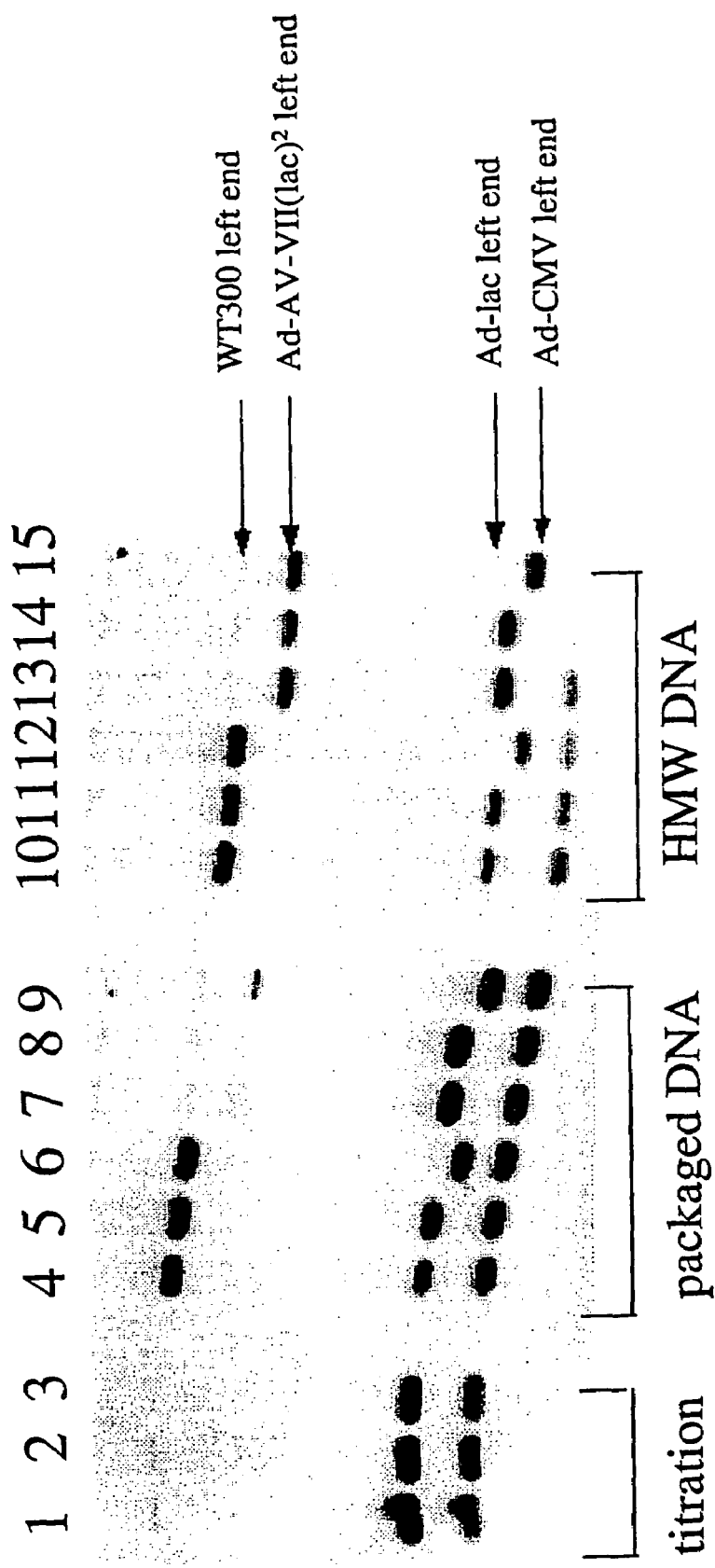

FIG. 8 is a Southern blot analysis of total nuclear DNA (HMW DNA) and virion DNA (packaged DNA) isolated from 293 cells coinfected with the Ad-AV-VII(lac)$^2$ virus (lanes 7-9 and 13-15) or Ad-WT300 (lanes 4-6 and 10-12) and Ad-LacWT (lanes 7 and 13), Ad-LacX86 (lanes 8 and 14), or Ad-CMV (lanes 9 and 15). Southern blot analysis was performed as described in Example 1. Fragments representing the left end termini of the different viruses are indicated by arrows to the right of the blot. A titration curve of HMW DNA is included for accurate quantitation in lanes 1, 2 and 3 (titration). In lanes 1, 2 and 3, the amounts of digested HMW DNA are 100 ng, 75 ng and 50 ng, respectively. Coinfections included the following pairs of viruses: lanes 9 and 15, Ad-AV-VII(lac)$^2$ and AD-CMV; lanes 8 and 14, Ad-AV-VII(lac)$^2$ and Ad-LacX86; lanes 7 and 13, Ad-AV-VII(lac)$^2$ and Ad-LacWT; lanes 6 and 12, Ad-WT300 and Ad-CMV; lanes 5 and 11, Ad-WT300 and Ad-LacX86; and lanes 4 and 10, Ad-WT300 and Ad-LacWT.

Figure 9:
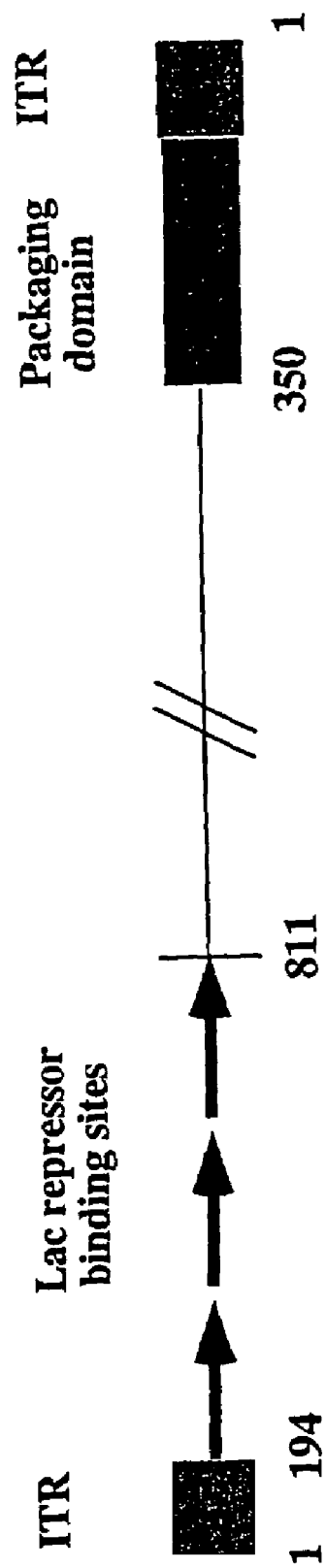

FIG. 9 is a schematic of Ad-lacsite$^3$/in340. The ITRs are indicated by squares, and the packaging domain located near the right terminus is indicated by a rectangle. The three lac binding sites at the left terminus are indicated by three arrows and were substituted in place of nts 194-811 deleting the natural packaging domain.

Figure 10:
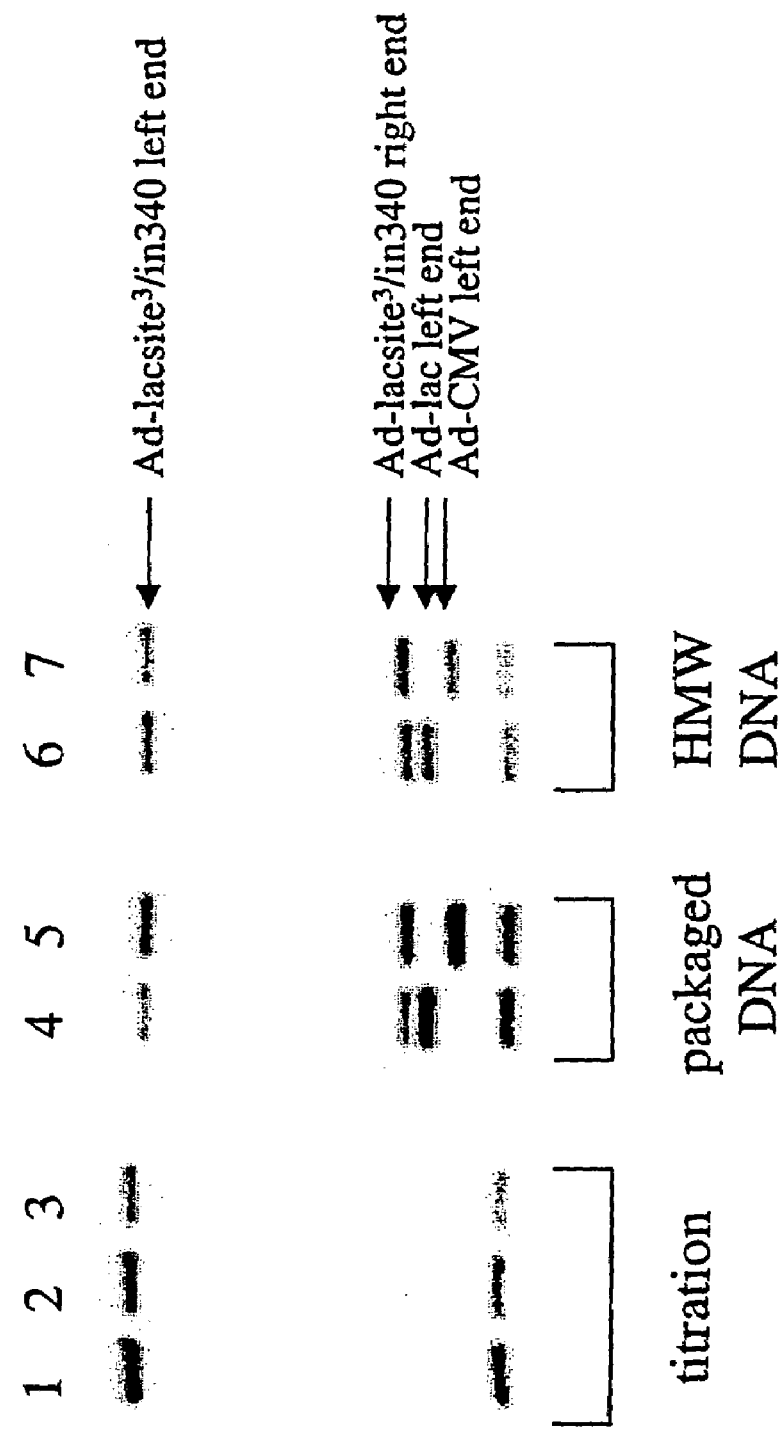

FIG. 10 is a Southern blot analysis of total nuclear DNA (HMW DNA) and virion DNA (packaged DNA) isolated from 293 cells coinfected with the Ad-lacsite$^3$/in340 virus (lanes 4-7) and Ad-LacWT (lanes 4 and 6) or Ad-CMV (lanes 5 and 7). Southern blot analysis was performed as described in Example 1. Fragments representing the left end termini of the different viruses are indicated by arrows to the right of the blot. A titration curve of digested HMW DNA is included for accurate quantitation in lanes 1, 2 and 3. In lanes 1, 2 and 3, the amounts of digested HMW DNA are 250 ng, 100 ng and 50 ng, respectively. Coinfections included the following pairs of viruses: lanes 4 and 6, Ad-lacsite$^3$/in340 virus and Ad-LacWT; lanes 5 and 7, Ad-lacsite$^3$/in340 virus and Ad-CMV.

Figure 11:
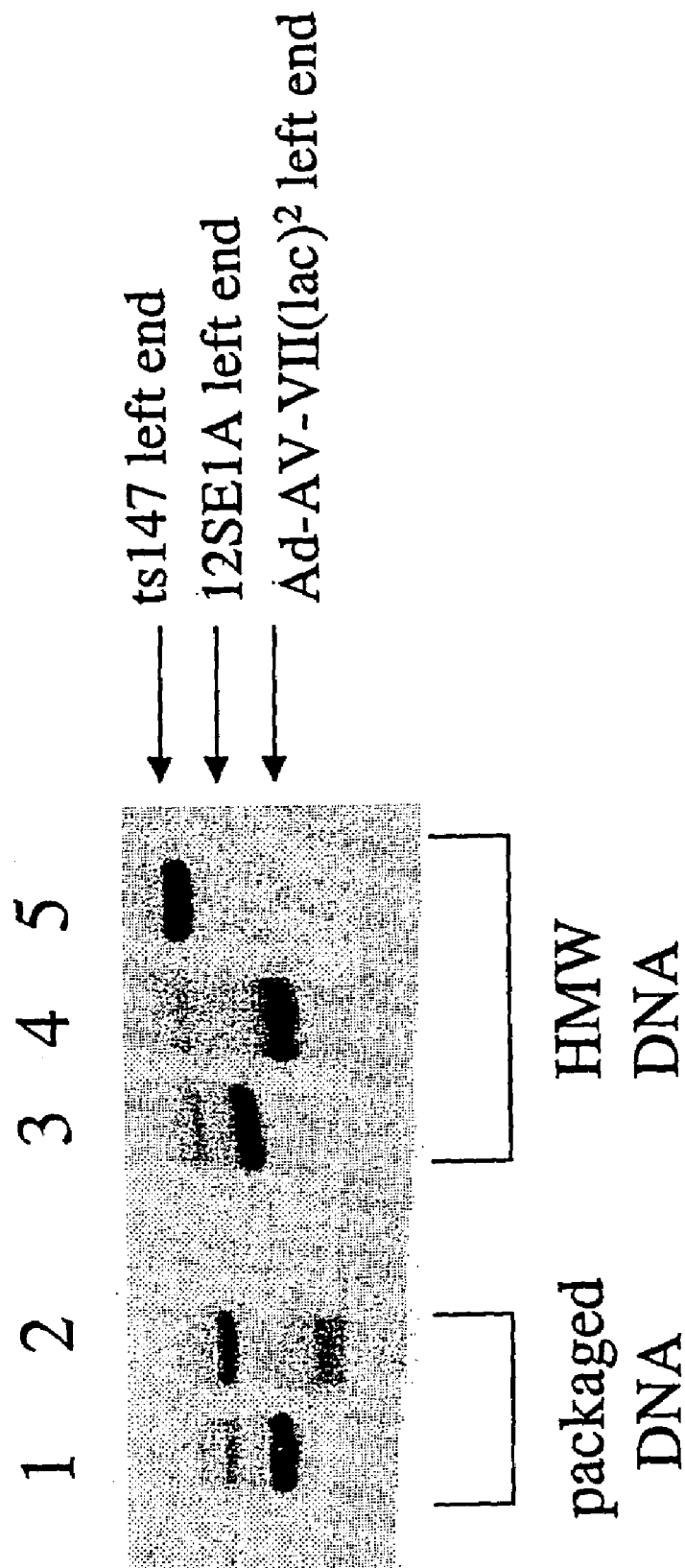

FIG. 11 is Southern blot analysis of total nuclear DNA (HMW DNA) and virion DNA (packaged DNA) isolated from 293 cells infected with the ts147 virus alone (lane 5) or ts147 virus coinfected with 12SE1A (lane 3) or Ad-AV-VII(lac)$^2$ (lane 4). Southern blot analysis was performed as described in Example 1. Fragments representing the left end termini of the different viruses are indicated by arrows to the right of the blot.

Figure 12:
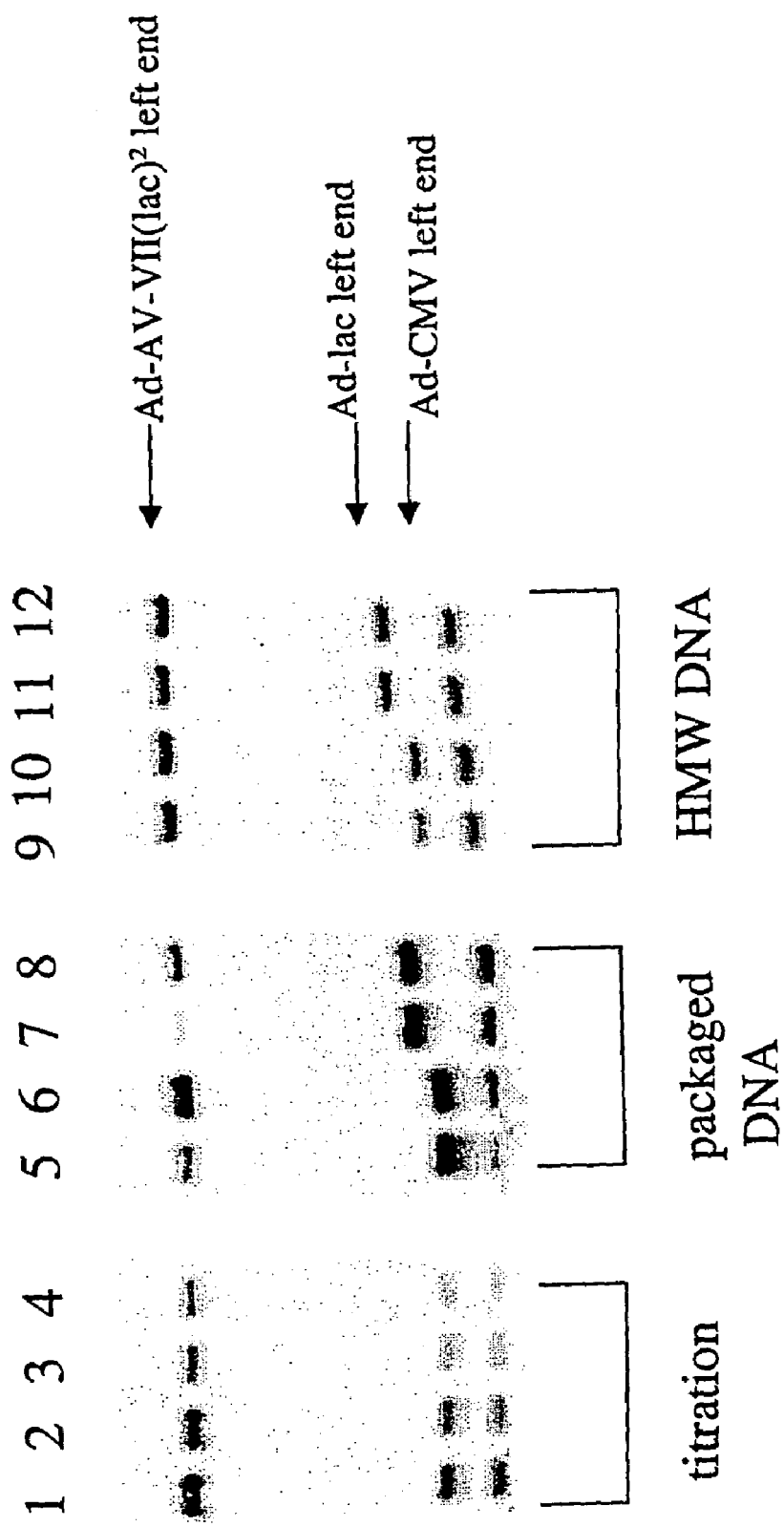

FIG. 12 shows a Southern blot analysis of total nuclear DNA (HMW DNA) and virion DNA (packaged DNA) isolated from 293 cells coinfected with the Ad-AV-VII(lac)$^2$ virus (lanes 5-12) and Ad-LacWT (lanes 7, 8, 11 and 12) or Ad-CMV (lanes 5, 6, 9 and 10), either in the absence of IPTG (lanes 5, 7, 9 and 11) or presence of 50 mM IPTG (lanes 6, 8, 10 and 12). Southern blot analysis was performed as described in Example 1. Fragments representing the left end termini of the different viruses are indicated by arrows to the right of the blot. A titration curve of HMW DNA is included for accurate quantitation in lanes 1 through 4. In lanes 1 through 4, the amounts of digested HMW DNA are 500 ng, 250 ng, 100 ng and 50 ng, respectively. Coinfections included the following pairs of viruses: lanes 5, 6, 9 and 10, Ad-AV-VII(lac)$^2$ and Ad-CMV; lanes 7, 8, 11 and 12 and 15, Ad-AV-VII(lac)$^2$ and Ad-LacWT.

Figure 13:
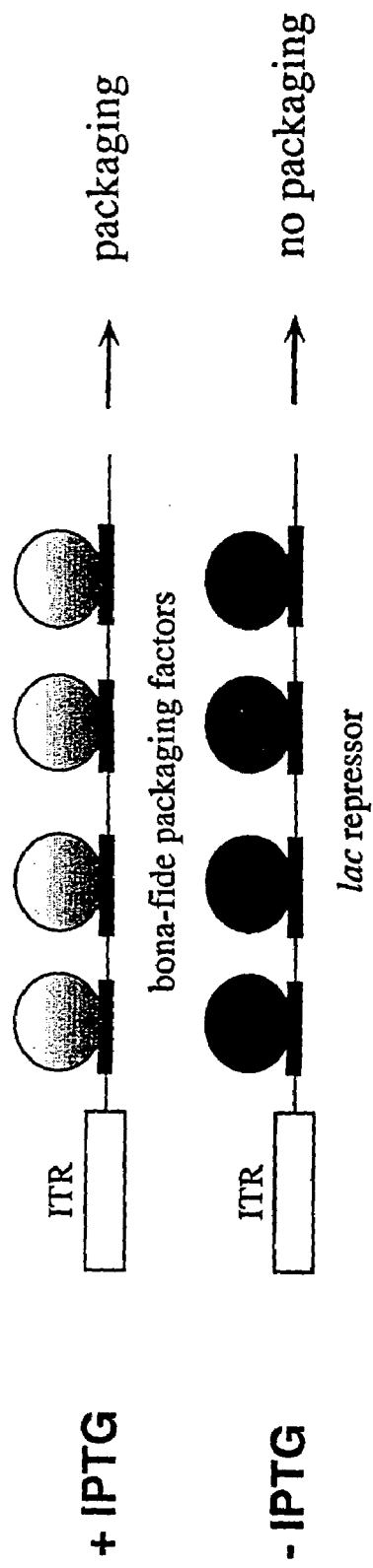

FIG. 13 is a schematic that depicts how the packaging of a helper virus may be selectively regulated by Lac repressor and IPTG. In the presence of IPTG (top), Lac repressor does not bind the packaging domain and the helper virus is packaged efficiently. In the absence of IPTG (bottom), Lac repressor binds the packaging domain and packaging domain and packaging is specifically repressed.

Figure 14:
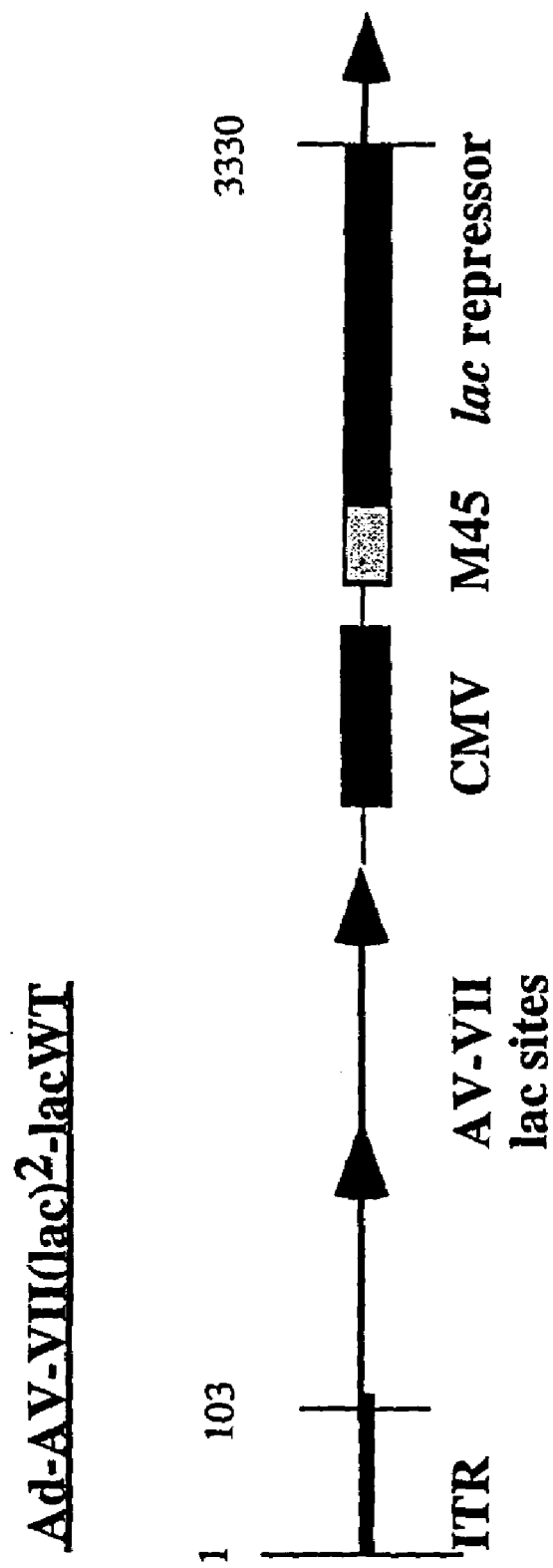

FIG. 14 is a schematic of the left-end of Ad-AV-VII(lac)$^2$-LacWT. The ITR is shown at the left end between nts 1 and 103. The AV-VII(lac)$^2$ dimer packaging domain is denoted by two arrows. The CMV-M45-Lac repressor cassette is denoted by rectangles.

Figure 15:
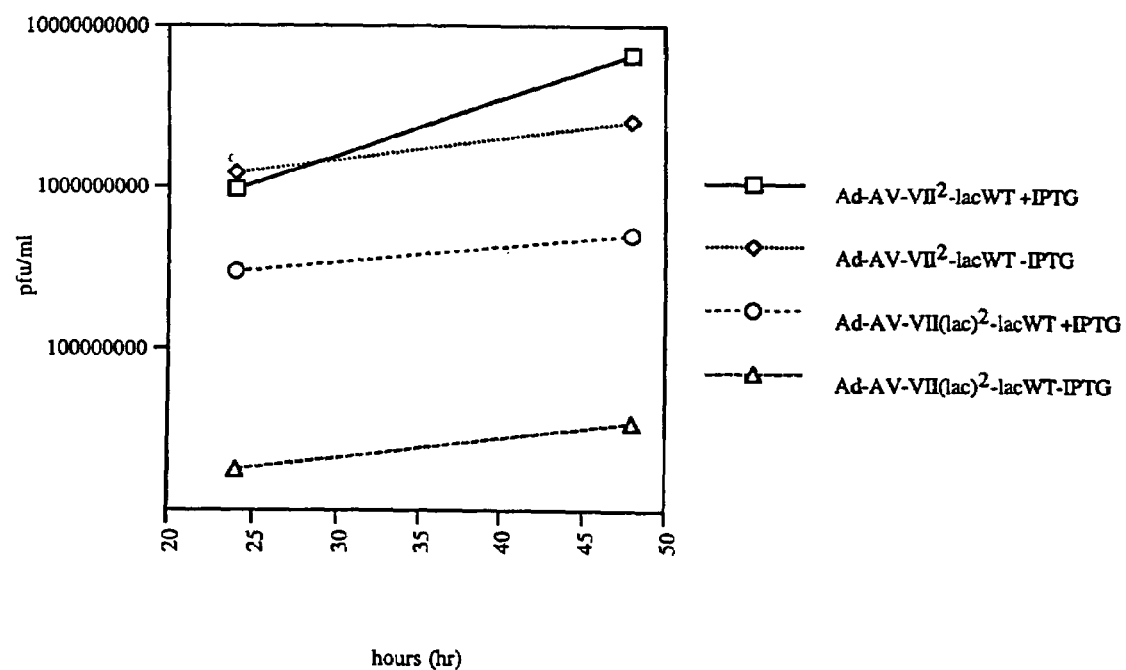

FIG. 15 shows the average of the results of three independent growth curve experiments performed in 293 cells in the presence or absence of IPTG with viruses Ad-AV-VII(lac)$^2$-LacWT and Ad-AV-VII$^2$-LacWT. Total cell lysates were prepared at 24 and 48 hr post-infection and virus yield was measured by duplicate serial dilution of infected cell lysates and plaque assay on 293 cells. The X axis represents time in hours (hr) and the Y axis represents virus yield measured as pfu/ml on a log scale.

DETAILED DESCRIPTION OF THE INVENTION

The present invention relates to recombinant Adenoviruses (Ad) which function as helper viruses to produce gutted Ad viruses lacking viral coding sequences. The recombinant helper Ad comprise a binding site for the *E. coli* Lac repressor protein embedded within the packaging domain. Available Lac repressor binds to its operator sites within the helper virus packaging domain, precluding the binding of natural packaging factors. The packaging of the subject helper viruses into virus capsids is specifically suppressed, in comparison to wild type (WT) Ad, in the presence of Lac repressor. The Ad helper viruses of the present invention regulate helper virus DNA packaging and may be used alone or in combination with the Cre-lox system of the prior art, to direct greater repression of packaging of Ad helper viruses.

As used herein, "gutted virus" or "gutted vector" means a virus deleted of most or all of its coding sequences. Gutted viruses or vectors may also be referred to as helper-dependent (HD), high capacity, or gutless.

Gutted Adenovirus vectors that lack all viral coding sequences are currently an important approach for gene therapy in order to minimize the host immune response to Ad infection by precluding the expression of Ad gene products. The production of gutted Ad vectors for gene therapy requires the use of a helper virus system where packaging of the helper virus genome into virus capsids is specifically suppressed, while the gutted Ad genome is efficiently packaged. For the production of the therapeutic gutted vector, the helper virus must provide early and late gene products for complementation in trans of the gutted virus.

In accordance with the present invention, packaging of the helper virus DNA genome is specifically suppressed via binding of Lac repressor to its binding sites within the packaging domain of this genome, while packaging of the therapeutic gutted vector is unhindered. For example, a recombinant Ad vector was constructed that harbors two binding sites for the E. coli Lac repressor protein embedded within the viral packaging domain. This virus, Ad-AV-VII(lac)$^2$, is infectious and able to provide helper function to a virus deficient in hexon capsomere assembly (Ad-ts147) (Kauffman and Ginsberg 1976). In a cotransfection experiment with an expression vector coding for Lac repressor, the DNA packaging of Ad-AV-VII(lac)$^2$ was suppressed by 2 orders of magnitude, in comparison to WT Ad, in the presence of Lac repressor. Normal levels of the Ad late protein penton were synthesized indicating that this repression was at the level of viral DNA packaging. In a coinfection experiment with a virus expressing Lac repressor (Ad-LacWT), the DNA packaging of Ad-AV-VII(lac)$^2$ was suppressed by 100-fold, in comparison to a coinfection of Ad-AV-VII(lac)$^2$ with Ad WT300.

For the production of an all-inclusive helper virus whose packaging is conditionally regulated by Lac repressor, the lac binding site-containing packaging domain and the Lac repressor coding sequences were combined within the same vector, designated Ad-AV-VII(lac)$^2$-LacWT. Since a constitutively active Lac repressor would block any DNA packaging and therefore prevent production of a virion stock of such a helper virus, Lac repressor activity should be regulated. One approach is to regulate Lac repressor activity and therefore DNA packaging of the Ad-AV-VII(ac)$^2$ virus by use of the inducer IPTG. To test regulation of Lac repressor activity via IPTG, the Ad-AV-VII(lac)$^2$ and Ad-Lac viruses were coinfected and incubated in media containing 50 mM IPTG or in media lacking IPTG. Results demonstrated that IPTG can indeed be used to regulate the DNA packaging of Ad-AV-VII (lac)$^2$.

The specificity of Lac repressor-mediated suppression of Ad-AV-VII(lac)$^2$ packaging was demonstrated. To show that the suppression observed was due specifically to the Lac repressor protein and the lac binding sites within the Ad-AV-VII(lac)$^2$ packaging domain, coinfection experiments were performed with viruses Ad-CMV and Ad-lacsite$^3$/in340. Within the Ad-lacsite$^3$/in340 genome, the packaging domain and lac binding sites are physically separated. The relative packaging efficiency of Ad-lacsite$^3$/in340 was not significantly affected by the presence of Lac repressor protein (Ad-LacWT), when compared to the packaging efficiency of Ad-lacsite$^3$/in340 DNA in a coinfection with a virus not expressing Lac repressor protein (Ad-CMV). This result indicates that Lac repressor protein can specifically inhibit the DNA packaging of a virus containing lac sites within its packaging domain by virtue of binding to these sites. The mechanism of suppression is likely steric hindrance by Lac repressor protein bound to the lac sites to preclude the binding of bona-fide Ad packaging factors.

An Ad whose DNA packaging is specifically suppressed while providing early and late gene products for complementation in trans of a gutted virus was also developed. To make such a Lac repressor/operator system, the Ad-AV-VII(lac)$^2$-LacWT virus was constructed. This virus contains two lac binding sites within the packaging domain, and expresses an M45-tagged Lac repressor under the control of a CMV promoter. So that DNA packaging of this virus is not constitutively suppressed, a means of regulation of the Lac repressor is provided that entails the inducer IPTG. Virus Ad-AV-VII (lac)$^2$-LacWT grown in media lacking IPTG was reduced for growth by ~20-fold compared to the growth of Ad-AV-VII (lac)$^2$-LacWT in media containing 50 mM IPTG. It should be noted, however, that this virus does not display wild type Ad growth characteristics even in the presence of 50 mM IPTG. The AV-VII(lac)$^2$ sequence does confer a disadvantage at some stage in virus growth when used as a packaging domain in vivo. A normal titer for wild type Ad5 when purified by CsCl centrifugation is $\geq 10^{12}$ particles/ml. A stock of purified Ad-AV-VII(lac)$^2$ or Ad-AV-VII(lac)$^2$-LacWT virions, however, generally has a titer of 1-3×10$^{11}$ particles/ml. The basis for this growth defect likely reflects an alteration in spacing between the two AV-VII repeat sequences. The insertion of the Lac repressor binding sites increased the spacing between the two AV-VII repeat sequences, compared to the two AV-VII repeat sequences that lack the Lac repressor binding sites. Even though the lac binding sites were integrated within the packaging genome without altering many nucleotides, the few nucleotide changes that were made may have been sufficient to interfere somehow with the binding of bona fide packaging factors. It should also be noted that the infectivity of CsCl-purified Ad-AV-VII(lac)$^2$-LacWT particles was not impaired. The particle to Pfu ratio for this virus was determined to be 8:1, similar to the ratio for a WT Ad (20:1). The particle to Pfu ratio for virus Ad-AV-VII$^2$-LacWT was determined to be 16:1. Lower particle to Pfu ratios reflect increased infectivity of a virus.

With respect to the utility of Ad-AV-VII(lac)$^2$-LacWT in a gene therapy setting, the reduced capabilities for growth of such a recombinant helper Ad, especially in a coinfection with another virus, confer an advantage. The growth of Ad-AV-VII(lac)$^2$-LacWT is affected by two levels of repression: an inherent disadvantage in a competition with other wild type packaging domains and the suppression of DNA packaging in the presence of Lac repressor protein. If employed as a helper virus to enable the growth of a gutted vector, the growth reduction phenotype of Ad-AV-VII(lac)$^2$-LacWT will result in an even lower level of contamination of helper virus in the gutted vector stock.

Thus in accordance with the present invention, there are provided recombinant helper Ad comprising trans-acting Ad sequences required for growth and assembly of a gutted Ad and at least one binding site for the Lac repressor located within the helper Ad packaging domain. A minimal packaging sequence of 5'-TTTGN$_8$CG-3' (SEQ ID NO:1) has recently been identified and designated as an A repeat. Preferably, the one or more lac binding sites is placed between the critical cis-acting A repeats. The cis-acting A repeats are fully described in copending U.S. patent application Ser. No. 09/530,935, which is incorporated by reference herein as if fully set forth. In a preferred embodiment, the recombinant helper Ad comprises at least two binding sites for the Lac repressor located within its packaging domain. In another preferred embodiment, a recombinant helper Ad comprising Lac repressor binding sites within its packaging domain and which also encodes the Lac repressor protein is provided. In growth curve experiments, the growth of such virus in medium lacking IPTG was reduced ~20-fold compared to growth in medium containing 50 mM IPTG. In addition, the virus displayed a ~5-fold reduction in growth in medium containing 50 mM IPTG compared to an analogous virus lacking the lac binding sites.

In a preferred embodiment, there is provided a recombinant helper Ad having one or more lac binding sites placed within the packaging domain and where in place of the E1 genes, there is located a Lac repressor coding sequence operatively linked to a promoter which functions in producer cells. For example, in addition to comprising one or more lac binding sites within the packaging domain, a CMV promoter/Lac repressor expression cassette may be located in place of one or both of the E1 genes. Alternatively, the Lac repressor expression cassette may be placed within one or both of the E1 genes, disrupting one or both of the E1 genes. The Lac repressor coding sequence may also be placed in another location in the Ad genome such as within or replacing the E3 or E4 regions. In addition to the CMV promoter, other promoters which function in producer cells may also be used to drive expression of the Lac repressor coding sequence. Examples include, but are not limited to, the SV40 or RSV promoter.

The recombinant helper Ad of the present invention can be constructed by standard recombinant DNA methods. Standard techniques for the construction of vectors are well-known to those of ordinary skill in the art and can be found in references such as Sambrook, Fritsch and Maniatis, 1989 or any of a number of laboratory manuals on recombinant DNA technology that are widely available. A variety of strategies are available for ligating fragments of DNA, the choice of which depends on the nature of the termini of the DNA fragments and can be readily determined by the skilled artisan. The recombinant vectors may then be subsequently rebuilt into intact viruses using standard methods such as that described in Stow 1981, which is incorporated by reference herein as if fully set forth. Other references which describe rebuilding recombinant vectors into intact viruses include Crouzet J, L. Naudin et al., 1997, which is also incorporated by reference herein as if fully set forth.

Since a constitutively active Lac repressor would block DNA packaging of a recombinant helper Ad and therefore prevent production of a virion stock of such a helper virus, Lac repressor activity should be regulated. In accordance with the present invention, the inducer IPTG may be used for such regulation. Thus, in the absence of IPTG, there is a suppress ion of DNA packaging of the recombinant helper Ad since available Lac repressor is bound to lac sites in the packaging domain of the recombinant helper Ad. Conversely, in the presence of IPTG, DNA packaging of the recombinant helper Ad ensues since the IPTG removes Lac repressor tetramers from the packaging domain of the recombinant helper Ad.

Other lactose derivatives may also be used to regulate Lac repressor in accordance with this invention. IPTG is a stable lactose derivative used widely in the literature, but lactose itself or other lactose derivatives may be used in place of IPTG. Examples of other lactose derivatives which may be used in accordance with the present invention, include but are not limited to: methyl 1-thio-β-D-galactoside, n-propyl 1-thio-β-D-galactoside, n-butyl β-D-galactoside, n-butyl 1-thio-β-D-galactoside, allolactose (6-O-β-galactopyranosyl-D-glucose, and thioallolactose [6(S)-galactopyranosyl-D-glucose (Barkley, Riggs et al., 1975).

In another aspect of the invention, there is provided a method for producing a gutted Ad substantially free of contaminating helper Ad. The method comprises the steps of (a) cotransfecting a producer cell(s) with (i) a gutted Ad vector, (ii) a recombinant helper Ad comprising trans-acting Ad sequences required for growth and assembly of a gutted Ad vector and at least one binding site for Lac repressor located within the packaging domain of the recombinant helper Ad, and (iii) a vector comprising coding sequence for Lac repressor protein operatively linked to a promoter which functions in the producer cell(s);

(b) growing the producer cells for a suitable time under conditions favorable for growth and packaging of the gutted Ad; and (c) suppressing packaging of the recombinant helper Ad by expression of the Lac repressor in the producer cells.

In another embodiment, a method for producing a gutted Ad substantially free of contaminating helper Ad comprises the steps of: (a) cotransfecting a producer cell(s) with: (i) a gutted Ad vector, (ii) a recombinant helper Ad comprising trans-acting Ad sequences required for growth and assembly of a gutted Ad vector and at least one binding site for Lac repressor located within the packaging domain of the recombinant helper Ad, wherein the recombinant helper Ad also comprises coding sequence for the Lac repressor operably linked to a promoter which functions in the producer cells;

(b) growing the producer cells for a suitable time under conditions favorable for growth and packaging of the gutted Ad; and (c) suppressing packaging of the recombinant helper Ad by expression of the Lac repressor in the producer cells.

In yet another embodiment of the invention, there is provided a method for producing a gutted Ad substantially free of helper Ad comprising the steps of: (a) cotransfecting a producer cell(s) with (i) a gutted Ad vector, (ii) a recombinant helper Ad comprising trans-acting Ad sequences required for growth and assembly of a gutted Ad vector and at least one binding site for Lac repressor located within the packaging domain of the recombinant helper Ad, wherein the producer cell(s) is capable of endogenous expression of the Lac repressor;

(b) growing the producer cells for a suitable time under conditions favorable for growth and packaging of the gutted Ad while suppressing packaging of the recombinant helper Ad by expression of the Lac repressor in the producer cell(s). In this aspect of the invention, expression of the Lac repressor in the producer cell(s) may be constitutive or inducible.

In another embodiment of the invention, the Ad packaging domain of the recombinant helper Ad may be regulated by a temperature shift. Thus, for example, producer cells cotransfected with a gutted Ad, a recombinant helper Ad with lac sites in the packaging domain and coding sequence for a temperature sensitive mutant of the Lac repressor (either in the recombinant helper Ad or in a separate expression vector) are grown at the permissive temperature for Lac repressor. This causes repression of the packaging of the helper virus by Lac repressor binding to lac sites in the packaging domain and allows growth and packaging of the gutted Ad vector which does not contain lac sites in its packaging domain. Where packaging of the helper virus is desired, the temperature is shifted to the restrictive temperature for Lac repressor, thereby inhibiting Lac repressor binding to lac sites. The coding sequences for temperature sensitive mutants of the Lac repressor have been published (Kleina and Mill, 1990)

and several mutants have been shown to function in a temperature-dependent manner in mammalian cells (Ward, Stover, et al 1995).

If regulation of packaging of the recombinant Ad vector is to be via temperature shift, then a temperature sensitive mutant coding sequence for the Lac repressor is employed.

Preferably, the gutted Ad further comprises a nucleotide sequence for a heterologous protein such as a therapeutic protein useful for the treatment of disease by gene therapy.

After construction of the recombinant helper Ad of the present invention, the Ad may be transfected into suitable producer cells. Such cells are known and include, for example, different E1-complementing cell lines such as 911 cells (Fallaux, Kranenburg et al., 1996), PER cells (Fallaux, Bout et al. 1998), A549-E1 cells (Imler, Chartier et al. 1996), HER-E1 cells (Gallimore, Grand and Byrd, 1986), N52.E6 (Schneider, Hertel et al. 2000) and KB-E1 cells (Babiss, Young et al., 1983).

The recombinant helper Ad of the present invention in the form of virions, may be used to coinfect suitable producer cells using standard techniques, at a multiplicity in the range of e.g., from about 10 to 10,000 particles per cell for a suitable time at a temperature of about 37° C. Preferably, a multiplicity is in the range of from about 50 to about 500 particles/cell. Most preferably, a multiplicity in the range of from about 100 to about 400 particles/cell is employed.

Recombinant helper Ad lysate stocks may be generated by growing in suitable producer cells in a medium containing IPTG at a concentration in the range of from about 0.10 mM IPTG to about 1.0M IPTG. Preferably, the IPTG concentration is in the range of about 2-50 mM IPTG. Lactose and other lactose derivatives may also be used in the same or similar range of concentration. Viruses may be amplified and titered in the same suitable cell line. Recombinant helper Ad produced from the transfected cells in the form of virions, may be harvested by standard methods. For example, infected cell lysates may be prepared by suspension of cells in a buffered saline solution followed by repeated freeze-thaw cycles and centrifugation at about 4,000×g at about 4° C. for a short period, such as e.g., 10 minutes. Titers may be determined e.g., by standard plaque assays using suitable cells.

The present invention also provides methods for producing a subject recombinant helper Ad. In one embodiment, the method comprises transfecting a producer cell(s) with a subject recombinant helper Ad hereinbefore described, and growing the producer cells for a suitable time in the presence of lactose or a lactose derivative. Examples of lactose derivatives include but are not limited to methyl 1-thio-β-D-galactoside, n-propyl 1-thio-β-D-galactoside, n-butyl β-D-galactoside, n-butyl 1-thio-β-D-galactoside, allolactose (6-O-β-galactopyranosyl-D-glucose), thioallolactose (6(S)-galactopyranosyl-D-glucose), and isopropyl-β-D-thiogalactopyranoside (IPTG).

Where a subject recombinant helper Ad comprises a temperature sensitive mutant coding sequence for Lac repressor, a method for producing such recombinant helper Ad comprises transfecting a producer cell(s) with the Ad and growing the producer cells for a suitable time at a restrictive temperature for the Lac repressor. The recombinant helper Ad of the present invention may be produced in a same producer cell as a gutted Ad vector. Alternatively, the recombinant Ad of the present invention may be produced separately, in a different producer cell than the gutted Ad vector. For example, when producing a lysate stock of a recombinant helper Ad of the present invention, the helper Ad may be grown without a gutted Ad vector. Alternatively, a producer cell may be first transfected with a recombinant helper Ad and grown in the presence of lactose or lactose derivative, or where appropriate, at a restrictive temperature for the Lac repressor. Once the producer cells are sufficiently stocked with helper Ad, the lactose or lactose derivative is no longer applied to the cells, e.g., no longer included in the culture media, or where appropriate, producer cells are grown at a permissive temperature for the Lac repressor. Gutted Ad added to these producer cells will be packaged by the recombinant helper Ad but the recombinant helper Ad will not package itself.

A method for suppressing packaging of helper Ad while packaging a gutted Ad vector is also provided by the present invention. The method comprises the steps of (1) cotransfecting a producer cell with (i) a gutted Ad vector, (ii) a recombinant helper Ad comprising trans-acting Ad sequences required for growth and assembly of a gutted Ad vector and at least one binding site for the Lac repressor located within the packaging domain of the recombinant helper Ad, and (iii) a vector comprising coding sequence for the Lac repressor protein, operatively linked to a promoter which functions in the producer cell; and (2) growing the producer cells for a suitable time under conditions favorable for growth and packaging of the gutted Ad vector while suppressing the packaging of the recombinant helper Ad by Lac repressor expression.

A vector comprising coding sequence encoding the Lac repressor protein, operatively linked to a promoter which functions in the producer cell, may be provided by a vector exogenously introduced into the producer cell, for example an adenovirus or other virus vector that expresses Lac repressor, or a plasmid vector that expresses Lac repressor. Alternatively, a producer cell line may be utilized that constitutively or inducibly expresses Lac repressor via an expression vector already contained within the producer cell line (i.e., endogenous Lac expression), for example Lac repressor expressed from coding sequences integrated into the producer cell line chromosomal DNA or carried on an extrachromosomal DNA episome.

Preferably, a method of suppressing packaging of helper Ad while packaging a gutted Ad vector comprises the steps of (1) cotransfecting a producer cell with: (i) a gutted Ad vector, (ii) a recombinant helper Ad comprising trans-acting Ad sequences required for growth and assembly of a gutted Ad vector and at least one lac binding site located within the packaging domain, and which also comprises coding sequence for the Lac repressor protein wherein the coding sequence is under the control of a promoter which functions in the target cells; and (2) growing the target cells for a suitable time under conditions favorable for packaging of the gutted Ad vector while suppressing the packaging of the recombinant helper Ad by Lac repressor expression. In a preferred embodiment, the coding sequence for the Lac repressor is located in an expression cassette placed in another part of the Ad genome such as the E1 or E3 region of the recombinant helper Ad. Examples of promoters which may be used to control expression of the Lac repressor protein include e.g., CMV, SV40 or RSV.

The present invention also provides a gutted Ad vector, essentially free (substantially free) of any contaminating helper virus, produced by any of the various methods of the invention herinbefore described. As used herein, "essentially free" means that a gutted Ad preparation contains less than or equal to 1% contaminating recombinant helper Ad. Preferably, a gutted Ad vector preparation does not contain any detectable recombinant helper Ad. In one embodiment of the invention, there is provided a gutted Ad expression vector, essentially free of any contaminating helper virus, produced by a method of (1) cotransfecting a producer cell with: (i) a gutted Ad vector, (ii) a recombinant helper Ad comprising trans-acting Ad sequences required for growth and assembly of a gutted Ad vector and at least one binding site for the Lac repressor located within the packaging domain of the recombinant helper Ad, and (iii) a vector comprising coding sequence encoding the Lac repressor protein, operatively linked to a promoter which functions in the producer cell; (2) growing the producer cells under conditions favorable for growth and packaging of the gutted Ad vector while suppressing the packaging of the recombinant helper Ad by Lac repressor expression, and (3) isolating the gutted Ad expression vector from the producer cells.

In still another embodiment, the present invention provides a gutted Ad vector, essentially free of any contaminating helper virus, produced by a method of (1) cotransfecting a producer cell with: (i) a gutted Ad vector, (ii) a recombinant Ad comprising trans-acting Ad sequences required for growth and assembly of a gutted Ad vector and at least one binding site for the Lac repressor located within the packaging domain, and which also comprises coding sequence for the Lac repressor protein wherein the coding sequence is under the control of a promoter which functions in the target cells; and (2) growing the target cells for a suitable time under conditions favorable for growth and packaging of the gutted Ad vector while suppressing the packaging of the recombinant helper Ad by Lac repressor expression, and (3) isolating the gutted Ad vector from the producer cells.

Gutted Ad vector may be isolated from producer cells using well known methods such as those described by William S. Wold (1999) Adenovirus Methods and Protocols, in *Molecular Medicine*, vol. 21, Humana Press, Totowa, N.J., the disclosure of which is incorporated by reference herein as if fully set forth.

The present invention further provides a kit having a container adapted to contain either the recombinant helper Ad or the gutted Ad vector of the present invention.

The following examples further illustrate the invention.

EXAMPLE I

Materials and Methods

Virus Constructions

Ad5 dl309, the parent for several recombinant viruses described herein, is a phenotypically wild-type virus that contains a unique XbaI cleavage site at 3.8 map units (Jones and Shenk 1979). Ad5 in340, the parent for recombinant virus Ad-lacsite$^3$/in340 is a dl309 derivative that carries the left-end 1-355 bp segment in place of the normal right-end terminal repeat (Hearing and Shenk 1983). Plasmid pE1A-194/811 contains the left-end Ad5 Xba1 fragment (nts 1 to 1339) with a deletion between nts 194-811 and a unique XhoI restriction site at the junction of the deletion. For the construction of the Ad-AV-VII$^2$ virus, a head to tail dimer of an oligonucleotide containing AV, AVI and AVII (5'-TCGACCGCG-TAATATTTGTCTAGGGCCGCGGG-GACTTTGACCGTTTACGTGGAGACTCC-3':5'TCGAG-GAGTCTCCACGTAAACGGTCAAAGTCCCCGCGGCC-CTAGACAAATATTACGCGG-3' (SEQ ID NO:2) was cloned into the 194/811 deletion (A repeats are underlined). For the construction of the Ad-AV-VII(lac)$^2$ virus, a head to tail dimer of an oligonucleotide containing AV, AVI, AVII and one *E. coli* Lac repressor binding site (5'-TCGACAATTGT-GAGCGCTCACAATTTGTCTAGGGC-CGCGGGGACTTTGACCGTTTACGTGGAGG-3':5'TC-GACCTCCACGTAAACGGTCAAAGTCCCCGCGGCC-TAGACAAATTGTGAGCGCTCACAATTG-3') (SEQ ID NO:3) was also cloned into the 194/811 deletion (A repeats are underlined and the lac site is bold-faced). Similarly, a head to tail trimer of an oligonucleotide containing the *E. coli* Lac repressor binding site (5'-TCGACAATTG TGAGCGCTCA-CAATTC-3':5'-GTTAACACTCGCGAGTGTTAAGAGCT-3') (SEQ ID NO:4) was cloned into the pE1A-194/811 background to construct virus Ad-lacsite$^3$/in340.

To construct Ad-LacWT, a virus expressing an M45-tagged, CMV promoter-driven *E. coli* Lac repressor protein, M45 and lacI sequence flanked by EcoRI ends was ligated to plasmid pXho-CMV, which contains Ad sequences 1-450 and 3330-5800 separated by the CMV promoter in a pBR322 backbone. Towards the construction of viruses that contain an AV-VII$^2$ or AV-VII(lac)$^2$ packaging domain as well as a Lac repressor expression cassette (viruses Ad-AV-VII$^2$-CMV-LacWT and Ad-AV-VII(lac)$^2$-LacWT), a PCR fragment of the packaging sequence dimer with an EcoRI end was generated. Next, a PCR fragment of the Lac repressor expression cassette with a KpnI end was generated. These two fragments were combined in a final PCR to yield one fragment containing the packaging sequence (in the 194/811 deletion background) upstream of the CMV-M45 Lac sequences flanked by EcoRI and KpnI ends. The resulting fragment was cloned into vector pXhoC-CMV. The recombinant plasmids were subsequently rebuilt into intact viruses by the method of Stow (Stow 1981). To generate stocks of these viruses, they were grown in 293 cells (Graham, Smiley et al. 1977) with IPTG in the media at a concentration of 2 mM. All constructs but the lac binding site trimer-containing plasmid were built into the dl309 background. The lac binding site plasmid was ligated to the right-end of virus in340. All viruses were amplified and tittered in 293 cells except viruses Ad-AV-VII$^2$-LacWT and Ad-AV-VII(lac)-LacWT. These viruses were plaque-purified and amplified in N52E.6 cells (Schiedner, Hertel et al. 2000) and titered in 293 cells. Viruses were screened by PCR of viral DNA obtained from infected cells by the Hirt procedure (Hirt 1967) and all insertions were verified by nucleotide sequence analysis of viral DNA obtained from CsCl purified virions.

Cultured Cells and Infections.

N52.E6 cells are human amniocyte cells transformed with Ad E1A and E1B sequences and were obtained from S. Kochanek (Center for Molecular Medicine, Cologne) (Schiedner, Hertel et al. 2000). Monolayer N52.E6 cells were maintained in alpha-minimal essential medium (CellGro) containing 10% fetal calf serum (HyClone) and 292 mg/l L-glutamine (Gibco). Agar overlays of N52.E6 cells for plaque assays were performed in 2XDME containing 5% fetal bovine serum (HyClone) and 0.1% yeast extract in water (Difco) combined with 1% agarose in water. Monolayer 293 cells were maintained in Dulbecco modified minimal essential medium containing 10% calf serum (HyClone). Virus lysate stocks were generated by four freeze-thaw cycles of infected cell lysates, and titers were determined by plaque assays on 293 cells. Virus infections were performed at a multiplicity of infection of either 100 or 200 particles/cell for one hr at 37° C. Fresh medium was added and the infected cells were maintained at 37° C. until the appearance of cytopathic effect (CPE), between 48-72 hrs post-infection. A stock of Ad5 ts147 (Kauffman and Ginsberg 1976) was generated following infection of 293 cells by maintenance of the infected cells at 32° C. until the appearance of CPE.

For the preparation of virions, infected cell lysates were prepared by suspension of cells in Tris-buffered saline solution followed by four freeze-thaw cycles and centrifugation at 4,000×g at 4° C. for 10 minutes. Purified virus particles were prepared by centrifugation over a CsCl step gradient (1.4 to 1.25 g of CsCl per cc). Particles were disrupted with sodium dodecyl sulfate (SDS) and centrifuged for five minutes at 13,000 g in a table-top microfuge. Virus particles were quantified by measurement of absorbance at 260 nm, assuming that 1 optical density unit at 260 nm is equivalent to $10^{12}$ particles. For coinfections, 293 cells were infected with viruses at 100 particles of each virus per cell, excluding the Ad-AV-VII(lac)$^2$ virus, which was used to infect cells with between 100 and 400 particles per cell. Coinfections were for one hr at 37° C. For the ts147 rescue experiment, plates were incubated at 39.5° C. subsequent to the one hr infection at 37° C. For coinfections with the virus containing a ts Lac repressor gene, plates were incubated at the permissive and non-permissive temperatures of 30° and 39.5° C., respectively, subsequent to the one hr incubation at 37° C. Virus particles were purified from coinfected cells as described above. Virus Ad-CMV, which is an E1A$^-$ and E1B$^-$ Ad containing the CMV promoter, was used as a negative control in the Ad-AV-VII(lac)$^2$ packaging suppression experiments. Virus Ad-12SE1A grows to nearly WT levels and was used as a positive control in the ts147 rescue experiment. For viral growth curve experiments, monolayer cultures of 293 cells were grown to approximately 85% confluency and infected with CsCl purified virions at 100 particles per cell for one hour at 37° C. The cells were then washed twice with Tris-buffered saline solution and fresh media was added. In some experiment sets, IPTG was used to enable the growth of virus Ad-AV-VII(lac)$^2$-CMV-LacWT at a concentration of 50 mM in the media. Total cell lysates were prepared at 24 and 48 hours post-infection by freeze-thawing of infected cells in culture medium, and virus yield was measured by duplicate serial dilution of infected cell lysates and plaque assay on 293 cells. Particle to PFU ratios were also determined by serial dilution of CsCl purified virions and plaque assay on 293 cells.

Determination of Packaging Efficiencies.

To determine the reduction of packaged DNA of recombinant viruses relative to WT virus, total replicated DNA as well as packaged viral DNA was isolated from 293 cells after a 48-72 hr coinfection. For the preparation of total nuclear DNA (HMW DNA), approximately 8×10$^6$ cells (less than half of one 100 mm plate) in media were processed using an adapted protocol from Sambrook, Fritsch and Maniatis (1989). The remaining cells from five 100 mm plates were used for the isolation of viral DNA. These cells were pelleted, lysed by four rounds of freeze/thawing and layered on two CsCl gradients. Viral DNA was prepared from purified virions as described previously (Graeble and Hearing 1992). Mutant and WT DNA were distinguished by restriction digestion (BamHI and HindIII) and their relative amounts were quantitated by Southern blot analysis (Maniatis, Fritsch et al. 1982). An approximately 200 nucleotide (nt) PCR product from pE1A-194/811 that hybridizes with the left end of Ad DNA (nts 1-194) was used as probe for hybridization. This DNA probe was labeled using the AlkPhos Direct labeling system (Amersham, Pharmacia Biotech, Piscataway, N.J.). Labeling occurs via the covalent attachment of alkaline phosphatase molecules to the DNA. Filters from the hybridizations were incubated with a fluorescent substrate for alkaline phosphatase, ATTOPHOS (JBL Scientific Inc./Promega, Madison, Wis.) and the substrate yields a fluorescent product upon cleavage by alkaline phosphatase. The signals were imaged on a Molecular Dynamics Storm860 phosphoimager (Molecular Dynamics, Sunnyvale, Calif.) and quantified using ImageQuant software version 1.2 (Molecular Dynamics). A titration of Ad-AV-VII(lac)$^2$ viral DNA was included in each blot to insure that the fluorescent signals obtained were in the linear range of the assay. Packaging efficiencies of the recombinant viruses were determined by quantifying the relative amounts of packaged DNA isolated from purified virus particles in comparison to the relative amounts of total nuclear viral DNA, as described previously (Schmid and Hearing 1997). The replication ratio is expressed as the replicated DNA signal from the Ad-AV-VII(lac)$^2$ virus divided by the sums of replicated DNA signals of the Ad-AV-VII (lac)$^2$ virus plus the different viruses used in coinfections. The virus packaging ratio is expressed as the packaged DNA signal from the Ad-AV-VII(lac)$^2$ virus divided by the sums of the packaged DNA signals of the Ad-AV-VII(lac)$^2$ virus plus the different viruses used in coinfections. The percent packaging efficiency of the Ad-AV-VII(lac)$^2$ virus was then determined by dividing the virus packaging ratio by the virus replication ratio.

EXAMPLE 2

DNA packaging of a recombinant Ad with *E. coli* lac binding sites embedded within the packaging domain is suppressed by the expression of Lac repressor protein.

Figure 2:
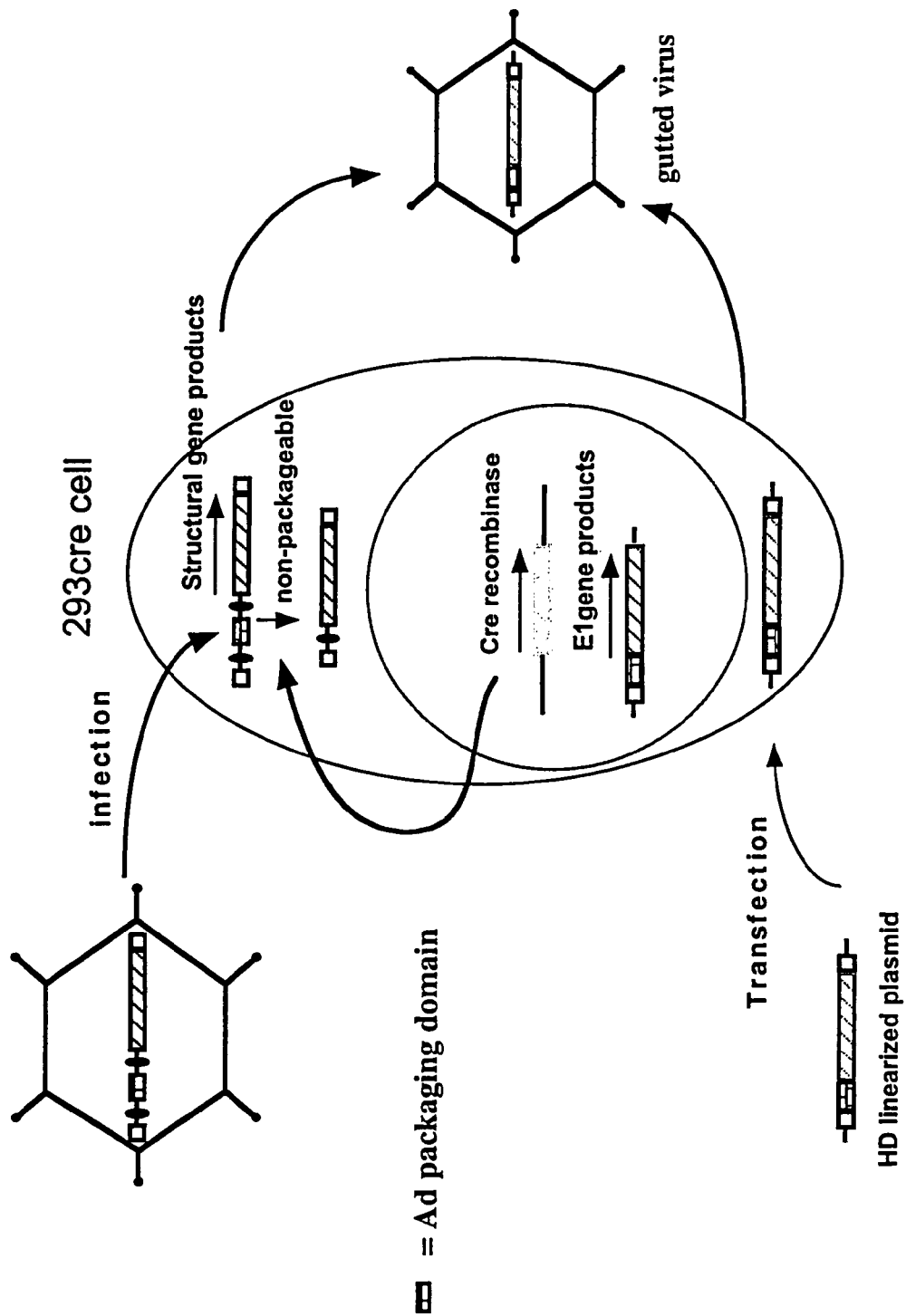
FIG. 2 is a schematic illustrating the propagation of gutted Ad vectors using the Cre-lox system of the prior art (Parks, Chen et al. 1996; Hardy, Kitamura et al. 1997).

The production of gutted Ad vectors for gene therapy requires the use of a helper virus system where packaging of the helper virus genome into virus capsids is specifically suppressed, while the gutted Ad genome is efficiently packaged (FIG. 1). Perhaps the host efficient helper system currently available is the Cre-lox system (FIG. 2) (Parks, Chen et al. 1996; Hardy, Kitamura et al. 1997). In this system, the helper virus has a packaging sequence flanked by loxP recognition sites. In 293 cells expressing Cre recombinase from bacteriophage P1, the packaging signal is excised, rendering the helper virus DNA unpackagable. Large scale preps of gutted virus produced by this method have shown ~1% contamination by the helper virus.

Towards the development of an optimized helper virus that can efficiently produce high-titer, uncontaminated stocks of gutted vectors, the *E. coli* Lac repressor and operator system has been exploited. The *E. coli* Lac repressor protein mediates the bacterium's ability to utilize lactose as an alternate source of energy in response to certain environmental stimuli (Silverstone, A. E., B. Magasanik et al. 1969). The 38 kDa Lac repressor protein binds as a tetramer to both lactose analogues as well as a cognate lac operator sequence. This protein acts to prevent transcription of the lac operon while bound to the operator sequence. However, when bound to the non-hydrolyzable lactose analogue isopropyl-β-D-thiogalactoside (IPTG), the Lac repressor binds with several hundred-fold lower affinity to the operator (Barkley M. D., A. D. Riggs et al. 1975), allowing transcription of the operon. This protein is composed of three domains: a 59 aa N-terminal DNA binding domain, a 270 aa domain dimerization and inducer binding domain (Muller-Hill 1975) and a 30 aa C-terminal leucine mini zipper domain that mediates tetramer assembly (Alberti, Oehler et al. 1991). The DNA binding N-terminus contains a helix-turn-helix motif (Lamerichs, Boelens et al. 1989) and recognizes an operator sequence of imperfect dyad symmetry, 5'-AATTGTGAGCGGATAACAATT-3' (SEQ ID NO:5) (Gilbert and Maxam 1973). The Lac repressor has been shown to bind with a 10-fold greater affinity to an artificial lac operator sequence that is perfectly symmetrical (Barkley and Bourgeois 1980).

Figure 3:
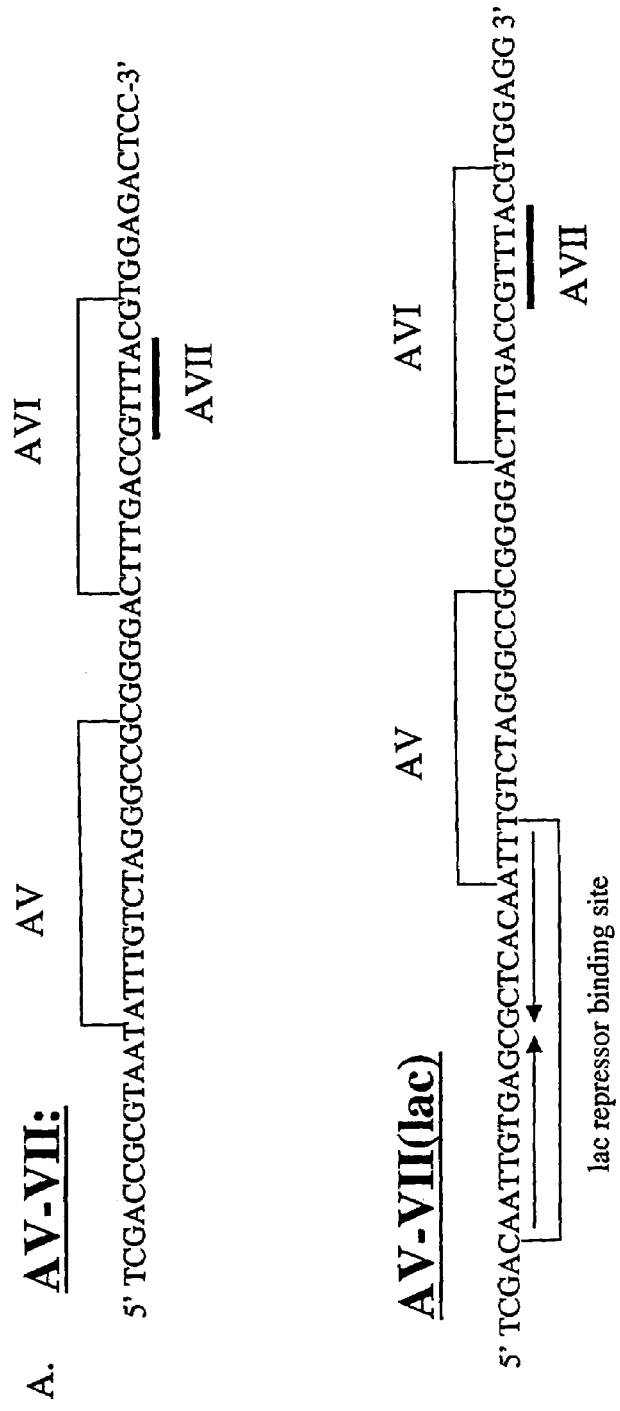
FIG. 3A is a schematic showing the nucleotide sequence of AV-VII (SEQ ID NO:6) and AV-VII(lac) (SEQ ID NO:7) packaging domains. The Lac repressor binding site within AV-VII(lac) is underlined and denoted by two arrows.
FIG. 3B is a schematic showing the Ad-AV-VII(lac)$^2$ virus with the AV-VII(lac) dimer packaging domain (denoted by two arrows) substituted for Ad nucleotides (nts) 194-811.
Figure 3:
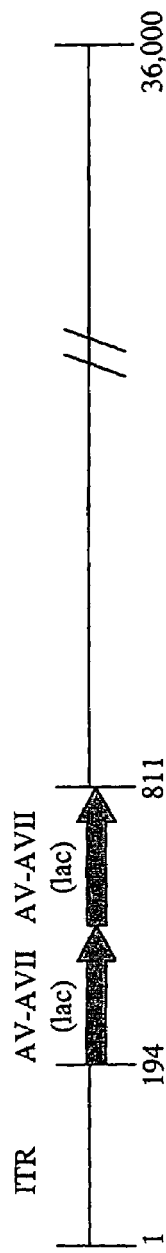

To explore whether or not viral DNA packaging could be regulated using the Lac repressor/operator system, a virus was constructed that contains two lac binding sites (perfectly symmetrical artificial site) within the packaging domain. Into a packaging domain deletion background, a dimer of A repeats V, VI and VII was inserted as the packaging domain. The AV-VII$^2$ sequence was chosen as it was shown to confer WT levels of DNA packaging in vivo (Schmid and Hearing 1998). This minimal domain dimer differs from the previously described AV-VII$^2$ domain, however, as it contains a Lac repressor binding site that begins upstream of A repeat V and overlaps with three nucleotides of AV. The resultant virus, known as Ad-AV-VII(lac)$^2$, therefore contains two lac binding sites nestled within the packaging domain (FIG. 3). It was postulated that the Lac repressor would bind to its binding sites embedded within the packaging domain and block DNA packaging by precluding the binding of natural packaging factors required for the packaging process.

To test first what effect the expression of Lac repressor protein would have upon the growth of this virus, viral DNA was cotransfected into cells with an M45-tagged Lac repressor expression vector. We predicted that virus growth would decrease upon increasing concentrations of the M45-Lac repressor expression plasmid, due to the binding of Lac repressor to the packaging domain and precluding the binding of natural packaging factors. The transfections were performed in 293 cells with either the M45-Lac expression vector, pCMX-M45-Lac, or an analagous vector lacking the Lac repressor sequence (pCMX) as a negative control. Each transfection also contained 2.7 µg of Ad-AV-VII(lac)$^2$ viral DNA. Increasing concentrations of the expression vectors were used: 0.1 µg, 0.2 µg, 0.5 µg and 1.0 µg. Two days post-infection, the cells were harvested and cellular lysates used to infect 293 cells to determine virus yield by plaque assay. The results of the plaque assay showed an approximately 1.5 log decrease in Ad-AVI-VII(lac)$^2$ virus yield in the pCMX-M45-Lac cotransfection sample compared to the Ad-AV-VII(lac)$^2$ and pCMX cotransfection sample. The decrease in viral yield suggested a possible defect at the level of DNA packaging.

Figure 4:
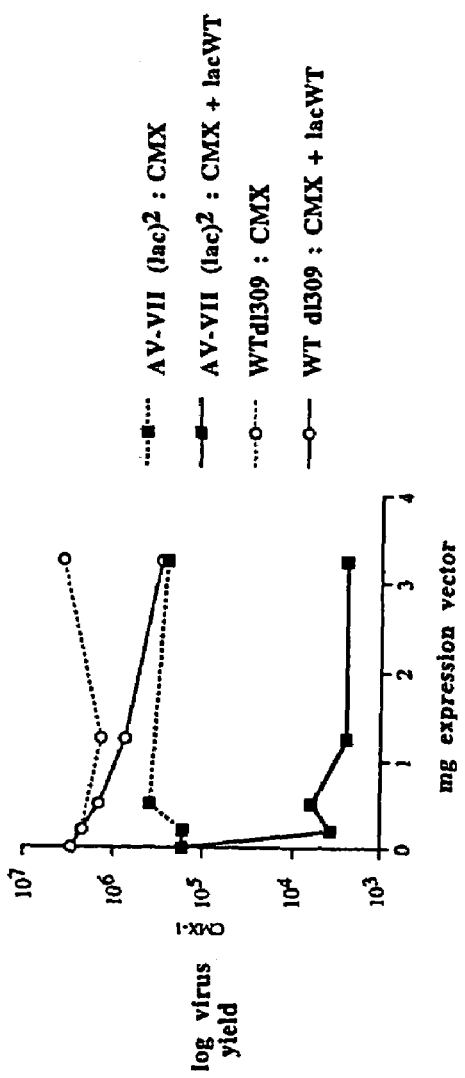
FIG. 4 graphically depicts results of a cotransfection experiment of Ad-AV-VII(lac)$^2$ and WT dl309 viral DNAs and plasmids pCMX and pCMX-M45-LacWT. The X axis represents increasing amounts of expression vector (μg expression vector) and the Y axis represents virus yield on a log scale as measured by plaque assay (data presented as log virus yield).

This experiment was subsequently modified and repeated. In addition to the Ad-AV-VII(lac)$^2$ viral DNA, WT dl309 viral DNA was also included in the cotransfections as a negative control. The two expression vectors, pCMX and pCMX-M45-LacWT were transfected at increasing concentrations: 0.2 µg, 0.5 µg, 1.25 µg and 3.125 µg. The viral DNAs were cotransfected at 2.8 µg per sample. The cells were harvested as described for the above experiment and virus yield was titered by plaque assay. In addition, western blotting of samples was performed with polyclonal rabbit antibodies to penton to examine levels of this late protein. The results of the plaque assay showed an approximately 2-log decrease in yield of the Ad-AV-VII(lac)$^2$ virus from the pCMX-M45-LacWT (0.5 µg) cotransfection, compared to the Ad-AV-VII (lac)$^2$ and pCMX cotransfection (FIG. 4). The anti-penton western blot showed nearly normal levels of penton expression, indicating that the decrease in virus yield was not due to a defect in transcription replication or translation. The results of the plaque assay and western blot were consistent with a defect in viral DNA packaging.

To determine if the M45-Lac repressor protein was capable of binding to the AV-VII(lac)$^2$ sequence used as a packaging domain in the Ad-AV-VII(lac)$^2$ virus, gel shift assays were performed. To generate a source of M45-Lac protein, 293 cells were transfected with pCMV-M45-LacWT as well as an expression vector coding for a mutant form of Lac repressor, pCMX-M45-LacX86. The X86 mutant contains a serine to leucine exchange at amino acid 61 and displays an in vitro binding constant to lac operator DNA of $10^{-15}$ M, 40-fold higher than that of WT Lac repressor (Chamness and Willson 1970; Jobe and Bourgeois 1972; Pfahl 1976; Schmitz, Coulondre et al. 1978). Whole cell extracts (W.C.E.) were prepared from 293 cells 48 hrs after transfection with these expression plasmids. The two probes used in the gel shifts were a monomer of the Lac repressor binding site and an AV-VII(lac)$^2$ dimer. Lac site monomer (FIG. 5A) and AV-VII (lac) dimer binding activities were detected in both extracts (FIG. 5B). In lane 1 of each gel, WCE was added to the binding reactions. In lane 2 of each gel, the monoclonal antibody M45 was added after a 30 min binding reaction with mock W.C.E. and incubation was then continued for an additional 30 min. In lanes 3 and 5 of each gel, LacWT and LacX86 W.C.E.s, respectively, were added to the binding reactions. These complexes were supershifted upon the addition of antibody M45 (lanes 4 and 6, FIGS. 5A and 5B respectively).

In order to confirm results from the Ad-AV-VII(lac)$^2$ and pCMX-M45-LacWT cotransfection, repression of DNA packaging by Lac repressor was measured using virus coinfections rather than DNA cotransfections. The degree to which the M45-Lac repressor protein is expressed was also anticipated to be much higher when the protein is encoded by a replicating virus, rather than by an expression vector. To this end, two viruses were constructed that encoded M45-LacWT and M45-LacX86 proteins, Ad-LacWT and Ad-LacX86 respectively (FIG. 6). These viruses contain a CMV-M45-Lac cassette in place of the viral E1A and E1B regions (nts 420-3330) as well as a WT packaging domain (nts 1-420).

To determine if a virally expressed Lac repressor protein would suppress the packaging of a second virus containing lac binding sites within the packaging domain, a coinfection of viruses Ad-AV-VII(lac)$^2$ and Ad-Lac (WT and X86 forms) was performed. The Ad-AV-AVII(lac) virus was also coinfected with Ad-CMV (containing an analagous CMV-M45 cassette minus Lac repressor coding sequence) as a negative control for the suppression of viral DNA packaging. Ad-WT300 (wild type adenovirus) does not contain Lac repressor binding sites within its packaging domain and was coinfected with viruses Ad-LacWT, Ad-LacX86 and Ad-CMV as a control for the lac site requirement. 293 cells were infected with 400 particles per cell of the Ad-AV-VII(lac)$^2$ virus and 100 particles per cell of the coinfecting virus. Six 100 mm plates were infected per experimental set. Once cells showed complete CPE (approximately 36-72 hrs post-infection), they were harvested and divided into two samples to prepare total nuclear DNA and viral DNA from purified virus particles. The HMW DNA represents the total pool of replicated DNA, while the DNA obtained from the purified virions represents that DNA which was packaged from the total pool of replicated DNA (FIG. 7). Both HMW and particle DNAs were digested with BamHI and HindIII to distinguish between coinfecting viruses and analyzed by Southern blot hybridization (Maniatis, Fritsch et al. 1982).

The Southern blot analyses to determine relative packaging efficiencies were performed using a DNA fragment of Ad nts 1-194 as probe. Quantification was performed using ImageQuant software (Molecular Dynamics). The Southern blot assay exhibits a 100-fold range of detection, from approximately 5 ng to 500 ng of full-length viral DNA. A titration of Ad-AV-VII(lac)$^2$ viral DNA was included on each blot to insure that the fluorescent signals obtained were in the linear range of the assay. Packaging efficiencies of the Ad-AV-VII(lac)$^2$ virus were determined by quantifying the relative amounts of packaged DNA isolated from purified virus particles in comparison to the relative amounts of total nuclear viral DNA, as described previously (Graeble and Hearing 1992). The replication ratio is expressed as the replicated DNA signal from the Ad-AV-VII(lac)$^2$ virus divided by the sums of replicated DNA signals of the Ad-AV-VII(lac)$^2$ virus plus the different viruses used in coinfections. The virus packaging ratio is expressed as the packaged DNA signal from the Ad-AV-VII(lac)$^2$ virus divided by the sums of the packaged DNA signals of the Ad-AV-VII(lac)$^2$ virus plus the different viruses used in coinfections. The percent packaging efficiency of the Ad-AV-VII(lac)$^2$ virus was then determined by dividing the virus packaging ratio by the virus replication ratio.

FIG. 8 shows a representative coinfection and Southern blot packaging assay to address the question of whether or not the Ad-AV-VII(lac)$^2$ genome is able to replicate normally and if its DNA packaging is specifically suppressed in the presence of Lac repressor protein. The Southern blot is divided into three sections: HMW DNA, packaged DNA, and a titration curve using a standard. The Ad nts 1-194 probe hybridizes to both ends of each viral genome, resulting in left and right end bands that correspond to each virus. The bands that correspond to the left-end fragments of the Ad-AV-VII(lac)$^2$ and coinfecting virus are those considered in the quantitation of replication and packaging efficiencies. The Ad-AV-VII(lac)$^2$ virus and coinfecting viruses replicated to comparable levels (lanes 13-15) as did wild type AdS (WT300; no lac sites) and the coinfecting viruses (lanes 10-12). Coinfection of WT300 with viruses that do or do not express Lac repressor had no or very little effect on WT300 viral DNA packaging (lanes 4-6). In marked contrast, coinfection of the Ad-AV-VII(lac)$^2$ virus with viruses that express Lac repressors resulted in very little or no detectable packaging of the Ad-AV-VII(lac)$^2$ viral DNA, whereas packaging of the coinfecting viral DNA was readily evident (lanes 7 and 8). The statistical results from three independent experiments are summarized in Table 1.

The top section of Table I summarizes results from coinfections of the Ad-AV-VII(lac)$^2$ virus with Ad-CMV, Ad-LacWT or Ad-LacX86. The lower section of the table summarizes results from coinfections of Ad-WT300 with Ad-CMV, Ad-LacWT or Ad-LacX86. Relative packaging efficiencies for Ad-AV-VII(lac)$^2$ DNA in coinfections with Ad-Lac were non-detectable (N.D.) in two experiments and 0.85% in a third experiment, all relative to the levels of Ad-CMV DNA packaging. Relative packaging efficiencies for Ad-AV-VII(lac)$^2$ DNA in coinfections with Ad-LacX86 were 1.5%, non-detectable and 0.55%. The coinfection of Ad-AV-VII(lac)$^2$ and Ad-CMV served as a control for the lac site requirement in packaging suppression. The results from these Southern blots showed that the Ad-AV-VII(lac)$^2$ was reduced for packaging in a coinfection with a virus that did not express Lac repressor; the average of three independent experiments was a packaging efficiency of 5.2%. Coinfections of Ad-WT300 and Ad-LacWT demonstrate that the expression of Lac repressor did not have a significant effect on the DNA packaging of Ad-WT300. The results of these experiments demonstrate that the Lac repressor specifically suppresses the packaging of the Ad-AV-VII(lac)$^2$ viral DNA.

Upon demonstrating the specific suppression of Ad-AV-VII(lac)$^2$ DNA packaging in the presence of Lac repressor protein, it was next important to address whether or not this was due specifically to the Lac repressor binding to the lac sites within the packaging domain. It was hypothesized that Lac repressor was suppressing DNA packaging by binding to lac sites within the packaging domain and sterically hindering the binding of bona-fide packaging factors to the packaging domain. It was possible, however, that the suppression of packaging was not directly due to the binding of Lac repressor to the packaging domain but to the binding of Lac repressor to the viral genome. To address this question, a virus was constructed that has a WT packaging domain at the right end of the genome, and contains three contiguous lac binding sites at the left end of the genome in place of the WT packaging domain (in340 background, FIG. 9). The goal was to separate the lac binding sites from the packaging domain and ask whether or not binding of Lac repressor to these sites at the left end interfered with DNA packaging or some other process required for viral growth. This virus, Ad-lacsite$^3$/in340 was coinfected with Ad-LacWT and assessed for DNA replication and packaging as described above (FIG. 10). Ad-lacsite$^3$/in340 was also coinfected with Ad-CMV as a control. Lane 4 shows the signals representing packaged DNA from an Ad-LacWT and Ad-lacsite$^3$/in340 coinfection. Lane 5 shows the signals representing packaged DNA from an Ad-CMV and Ad-lacsite$^3$/in340 coinfection. Lanes 6 and 7 show the signals representing replicated DNA that correspond to the coinfections of lanes 4 and 5, respectively. The results from four independent coinfection experiments of Ad-lacsite$^3$/in340 and Ad-LacWT or Ad-CMV are shown in Table 2.

The relative packaging efficiency of Ad-lacsite$^3$/in340 was not significantly affected by the presence of Lac repressor protein (Ad-LacWT), when compared to the packaging efficiency of Ad-lacsite$^3$/in340 DNA in a coinfection with a virus not expressing Lac repressor protein (Ad-CMV). This result demonstrates that Lac repressor protein specifically inhibited the DNA packaging of a virus containing lac sites within its packaging domain by virtue of binding to these sites.

EXAMPLE 3

The Ad-AV-VII(lac)$^2$ virus provides helper virus function to Ad mutant ts147.

Upon showing that the DNA packaging of the Ad-AV-VII(lac)$^2$ virus could be suppressed by the Lac repressor protein, it was next important to address the question of whether or not this virus could perform helper functions and rescue a mutant virus, properties required for gutted vector production. The prediction was that the Ad-AV-VII(lac)$^2$ virus would rescue a virus deficient in the production of necessary proteins, since Ad-AV-VII(lac)$^2$ codes for all proteins that a second virus would need to grow in 293 cells. To test this prediction, Ad ts147 was employed (Kauffman and Ginsberg 1976). At the non-permissive temperature of 39.5° C., ts 147 is unable to assemble a capsid due to the failure of the hexon protein to be transported into the nucleus. Ad ts147 was coinfected with the Ad-AV-VII(lac)$^2$ virus or Ad 12SE1A at the non-permissive temperature. Ad 12SE1A served as a positive control in this experiment; this virus displays WT growth in 293 cells, and it allowed for a distinction in mobilities of left-end fragments of Ad 12SE1 A and Ad ts147 in a digest with HindIII. A coinfection of the Ad-AV-VII(lac)$^2$ virus and Ad ts147 viruses at the non-permissive temperature resulted in encapsidated ts147 genomes (FIG. 11, lane 2), to a comparable extent as seen with the positive control E1A12S (lane 1). The signals in lanes 3, 4 and 5 represent replicated DNA in a ts147 and 12SE1A coinfection, ts147 and Ad-AV-VII(lac)$^2$ virus coinfection, and a ts147 infection, respectively. In duplicate experiments, the Ad-AV-VII(lac)$^2$ virus rescued the Ad ts147 phenotype by supplying WT hexon protein.

EXAMPLE 4

DNA packaging of the Ad-AV-VII(lac)$^2$ virus is regulated by IPTG in the presence of Lac repressor.

As a means to regulate Lac repressor activity and therefore DNA packaging of the Ad-AV-VII(lac)$^2$ virus, the inducer IPTG was employed. To test regulation of Lac repressor activity via IPTG, coinfections were performed with the Ad-AV-VII(lac)$^2$ virus and Ad-LacWT virus in the presence or absence of 50 mM IPTG. The predictions for this experiment were two-fold: 1) a suppression of the DNA packaging of the Ad-AV-VII(lac)$^2$ virus would be observed in the absence of IPTG since Lac repressor would be bound to the packaging domain, and 2) DNA packaging of this virus in the presence of IPTG, which removes Lac repressor tetramers from the packaging domain, would be observed by allowing the natural packaging factors to bind and packaging to ensue. An IPTG concentration of 50 mM was chosen, as it has been reported in the literature to effect maximum induction of chloramphenicol acetyl transferase (CAT) activity in a mammalian cell line containing an integrated CAT gene under control of a hybrid SV40 promoter bearing a lac operator (Figge, Wright et al. 1988). Coinfections of Ad-AV-VII(lac)$^2$ and Ad-LacWT viruses and subsequent analyses were performed as previously described in the Example 2.

FIG. 12 shows a representative southern blot of three independent experiments. The signals in lane 5 represent packaged DNA in a coinfection of Ad-AV-VII(lac)$^2$ and Ad-CMV viruses in the absence of IPTG. The signals in lane 6 represent packaged DNA in a coinfection of these two viruses but in the presence of 50 mM IPTG. The signals in lane 7 represent packaged DNA in a coinfection of Ad-AV-VII(lac)$^2$ and Ad-LacWT viruses in the absence of IPTG. The signals in lane 8 represent packaged DNA from a coinfection of these two viruses but in the presence of 50 mM IPTG. The signals in lanes 9 through 12 represent replicated DNA that corresponds to the coinfections described for lanes 5 through 8, respectively. The results of three experiments are summarized in Table 3. The packaging efficiency of Ad-AV-VII(lac)$^2$ in the presence of Lac repressor and 50 mM IPTG was 23%, 11% and 6% in three separate experiments. The packaging efficiency of Ad-AV-VII(lac)$^2$ in the presence of Lac repressor but with the absence of IPTG was non-detectable in all three experiments. In contrast, equivalent levels of DNA packaging of Ad-AV-VII(lac)$^2$ were observed with coinfection of Ad-CMV with or without the addition of IPTG. Thus, the effect of Lac repressor on the DNA packaging of the Ad-AV-VII(lac)$^2$ virus was dramatic and shown to be regulated by the inducer IPTG.

EXAMPLE 5

Construction of an all-inclusive helper virus containing an AV-VII(lac)$^2$ packaging domain and an M45-Lac repressor expression cassette.

These results demonstrated that packaging of a virus containing lac sites in the packaging domain could be selectively regulated by Lac repressor and the presence or absence of IPTG (FIG. 13). Towards the development of an all-inclusive helper virus whose packaging is specifically and selectively repressed while providing early and late gene products for complementation in trans of a gutted virus, the following recombinant Ad was constructed (FIG. 14). Ad-AV-VII(lac)$^2$-LacWT contains the AV-VII(lac)$^2$ minimal domain in place of the WT packaging domain as well as a CMV-M45-LacWT expression cassette. Ad-AV-VII$^2$-LacWT serves as a control, and contains the AV-VII$^2$ minimal domain without Lac binding sites, as well as the CMV-M45-LacWT expression cassette. These viruses were plaque purified and grown in N52.E6 cells. N52.E6 cells are a human amniocyte cell line transformed with Ad E1A and E1B sequences (Schiedner, Hertel et al. 2000). These cells contain only Ad nts 505-3522 and share no homologous sequence with the viral DNA constructs, thus eliminating the possibility of the generation of replication competent adenovirus (RCA) by recombination with Ad sequences present in other E1-containing cell lines. To generate stocks of these viruses, they were grown in N52.E6 cells with IPTG in the media at a concentration of 2 mM. IPTG is required in the media, as these viruses express Lac repressor protein that is able to bind to lac binding sites within the packaging domain and suppress packaging. From the literature on Lac repressor, a concentration of 2 mM has been shown to be effective in *E. coli* and mammalian cells. Results indicate that a 2 mM concentration allowed for growth of these viruses.

To analyze the growth characteristics of these viruses, growth curve experiments were performed in the presence and absence of IPTG. For viral growth curves, monolayer cultures of 293 cells were grown to approximately 85% confluency and infected with CsCl purified virions of Ad-AV-VII(lac)$^2$-LacWT or Ad-AV-VII$^2$-LacWT at 100 particles per cell for one hr at 37° C. The cells were then washed twice with Tris-buffered saline solution and fresh media was added. IPTG at a concentration of 50 mM in the media was used in one set of infections to enable the growth of virus Ad-AV-VII(lac)$^2$-LacWT. Total cell lysates were prepared at 24 and 48 hrs post-infection by freeze-thawing of infected cells in culture medium, and virus yield was measured by duplicate serial dilution of infected cell lysates and plaque assay on 293 cells. The average of the results of three independent viral growth curve experiments are shown in FIG. 15. With regard to the effects of IPTG on viral growth, the virus Ad-AV-VII$^2$-LacWT was used as a negative control, as there are no lac sites within the genome of this virus. The growth of virus Ad-AV-VII$^2$-LacWT was essentially unaffected by the presence of IPTG, as the virus yield was nearly equal for viruses grown in media with or without 50 mM IPTG. Even when grown in media containing 50 mM IPTG, the growth of virus Ad-AV-VII(lac)$^2$-LacWT was reduced 5 to 10-fold in comparison to the growth of virus Ad-AV-VII$^2$-LacWT in media containing 50 mM IPTG. Virus Ad-AV-VII(lac)$^2$-LacWT grown in media lacking IPTG was reduced for growth an additional 15 to 20-fold compared to the growth of Ad-AV-VII(lac)$^2$-LacWT in media containing 50 mM IPTG. Although titers of CsCl-purified virions were consistently lower for Ad-AV-VII(lac)$^2$-LacWT than for Ad-AV-VII$^2$-LacWT, the infectivity of the CsCl-purified Ad-AV-VII(lac)$^2$-LacWT virions was not impaired. Particle to Pfu ratios were determined for both viruses by serial dilution of CsCl-purified virions and plaque assay on 293 cells. The Ad-AV-VII$^2$-LacWT virus exhibited a particle to Pfu ratio of 16:1 (a ratio of 20:1 is observed with WT Ad) and the Ad-AV-VII(lac)$^2$-LacWT virus exhibited a ratio of 8:1. The lower levels of virus Ad-AV-VII(lac)$^2$-LacWT in the presence of 50 mM IPTG compared to the levels of virus Ad-AV-VII$^2$-LacWT may reflect an inherent disadvantage of the AV-VII(lac)$^2$ sequence as a packaging domain compared to the AV-VII$^2$ domain that has been shown to package at nearly WT levels (Schmid and Hearing 1997). The coinfection experiments with the Ad-AV-VII(lac)$^2$ virus described herein have revealed a competition event between the Ad-AV-VII(lac)$^2$ virus and the coinfecting virus, with Ad-AV-VII(lac)$^2$ consistently showing a disadvantage, regardless of the coinfecting virus used. Additionally, these results demonstrate that the inducer IPTG can act to regulate the DNA packaging of the Ad-AV-VII(lac)$^2$-LacWT virus that expresses the lac repressor protein.

REFERENCES

Addison, C. L., T. Braciak, et al. (1995). "Intratumoral injection of an adenovirus expressing interleukin 2 induces regression and immunity in a murine breast cancer model." *Proc Natl Acad Sci U S A* 92(18): 8522-6.

Addison, C. L., J. Gauldie, et al. (1995). *International J of Oncology* 7: 1253-1260.

Alberti, S., S. Oehler, et al. (1991). "Dimer-to-tetramer assembly of Lac repressor involves a leucine heptad repeat." *New Biol* 3(1): 57-62.

Babiss L E, Young C S, et al. (1983). "Expression of adenovirus E1a and E1b gene products and the *Escherichia coli* XGPRT gene in KB cells." *J Virol* 46(2):454-65.

Barkley M. D., A. D. Riggs et al. (1975). "Interaction of effecting ligands with lac repressor and repressor-operator complex." *Biochem* 14(8):1700-12.

Chamness G. C., and C. D. Willson. (1980). "An unusual lac repressor mutant." *J Mol Biol* 53(3):561-5.

Chen, H. H., L. M. Mack, et al. (1997). "Persistence in muscle of an adenoviral vector that lacks all viral genes." *Proc Natl Acad Sci U S A* 94(5): 1645-50.

Crouzet J., L. Naudin et al. (1997). "Recombinational construction in *Escherichia coli* of infectious adenoviral genomes." *Proc Natl Acad Sci U S A* 94(4):1414-9.

Fallaux F. J., A. Bout A, et al. (1998). "New helper cells and matched early region 1-deleted adenovirus vectors prevent generation of replication-competent adenoviruses." *Human Gene Therapy* 9(13):1909-17.

Fallaux F J, O. Kranenburg et al. (1996). "Characterization of 911: a new helper cell line for the titration and propagation of early region 1-deleted adenoviral vectors." *Human Gene Therapy* 7(2):215-22.

Figge, J., C. Wright, et al. (1988). "Stringent regulation of stably integrated chloramphenicol acetyl transferase genes by *E. coli* lac repressor in monkey cells." *Cell* 52(5): 713-22.

Gallimore P. H., R. J. Grand, and P. J. Byrd. (1986). "Transformation of human embryo retinoblasts with simian virus 40, adenovirus and ras oncogenes." *Anticancer Res* 6(3 Pt B):499-508.

Gaynor, R. B., L. T. Feldman, et al. (1985). "Viral immediate early proteins activate transcription of class III genes." *Science* 230: 447-450.

Gilbert, W. and A. Maxam (1973). "The nucleotide sequence of the lac operator." *Proc Natl Acad Sci U S A* 70(12): 3581-4.

Graeble, M. and P. Hearing (1990). "Adenovirus Type 5 Packaging Domain Is Composed of a Repeated Element That Is Functionally Redundant." *J Virol* 64(5): 2047-2056.

Graeble, M. and P. Hearing (1992). "Cis and trans requirements for the selective packaging of adenovirus type 5 DNA." *J Virol* 66(2): 723-731.

Graham, F. L., J. Smiley, et al. (1977). "Characteristics of a human cell line transformed by DNA from human adenovirus type 5." *J Gen Virol* 36: 59-72.

Hardy, S., M. Kitamura, et al. (1997). "Construction of adenovirus vectors through Cre-lox recombination." *J Virol* 71(3): 1842-9.

Hearing, P. and T. Shenk (1983). "The adenovirus type 5 E1A transcriptional control region contains a duplicated enhancer element." *Cell* 33: 695-703.

Hearing, P. and T. Shenk (1986). "The adenovirus type 5 E1A enhancer contains two functionally distinct domains: one is specific for E1A and the other modulates all early units in cis." *Cell* 45: 229-236.

Hirt B. (1967). "Selective extraction of polyoma DNA from infected mouse cell cultures." *J Mol Biol* 26(2):365-9.

Imler J. L., C. Chartier et al. (1996). "Novel complementation cell lines derived from human lung carcinoma A549 cells support the growth of E 1-deleted adenovirus vectors." *Gene Therapy* 3(1):75-84.

Jobe, A. and S. Bourgeois (1972). "The lac repressor-operator interaction. VII. A repressor with unique binding properties: the X86 repressor." *J Mol Biol* 72(1): 139-52.

Jones, N. and T. Shenk (1979). "An adenovirus type 5 early gene function regulates expression of other early viral genes." *Proc. Natl. Acad. Sci USA* 76: 3665-3669.

Kauffman, R. S. and H. S. Ginsberg (1976). "Characterization of a temperature-sensitive, hexon transport mutant of type 5 adenovirus." *J Virol* 19(2): 643-58.

Kleina. L. G. and J. H. Miller. (1990). "Genetic studies of the lac repressor. XIII. Extensive amino acid replacements generated by the use of natural and synthetic nonsense suppressors." *J Mol Biol* 212(2):295-318.

Kochanek, S., P. R. Clemens, et al. (1996). "A new adenoviral vector: Replacement of all viral coding sequences with 28 kb of DNA independently expressing both full-length dystrophin and b-galactosidase." *Proc Natl Acad Sci U S A* 93: 5731-5736.

Lamerichs, R. M., R. Boelens, et al. (1989). "NMR study of a complex between the lac repressor headpiece and a 22 base pair symmetric lac operator." *Biochem* 28(7): 2985-91.

Lusky, M., M. Christ, et al. (1998). "In vitro and in vivo biology of recombinant adenovirus vectors with E1, E1/E2A, or E1/E4 deleted." *J Virol* 72(3): 2022-32.

Morral, N., W. O'Neal, et al. (1999). "Administration of helper-dependent adenoviral vectors and sequential delivery of different vector serotype for long-term liver-directed gene transfer in baboons." *Proc Natl Acad Sci U S A* 96(22): 12816-21.

Morral, N., R. J. Parks, et al. (1998). "High doses of a helper-dependent adenoviral vector yield supraphysiological levels of alphal-antitrypsin with negligible toxicity." *Human Gene Therapy* 9(18): 2709-16.

Morsy, M. A., M. Gu, et al. (1998). "An adenoviral vector deleted for all viral coding sequences results in enhanced safety and extended expression of a leptin transgene." *Proc Natl Acad Sci U S A* 95(14): 7866-71.

Muller-Hill, B. (1975). "Lac repressor and lac operator." *Prog Biophys Mol Biol* 30(2-3): 227-52.

O'Neal, W. K., H. Zhou, et al. (1998). "Toxicological comparison of E2a-deleted and first-generation adenoviral vectors expressing alpha1-antitrypsin after systemic delivery." *Human Gene Therapy* 9(11): 1587-98.

Parks, R. J., L. Chen, et al. (1996). "A helper-dependent adenovirus vector system: removal of helper virus by Cre-mediated excision of the viral packaging signal." *Proc Natl Acad Sci U S A* 93(24): 13565-70.

Pfahl, M. (1976). "lac Repressor-operator interaction. Analysis of the X86 repressor mutant." *J Mol Biol* 106(3): 857-69.

Poller, W., S. Schneider-Rasp, et al. (1996). "Stabilization of transgene expression by incorporation of E3 region genes into an adenoviral factor IX vector and by transient anti-CD4 treatment of the host." *Gene Therapy* 3(6): 521-30.

Sambrook, J., E. F. Fritsch, and T. Maniatis. (1989) *Molecular Cloning: A Laboratory Manual*, Cold Spring Harbor Laboratory Press, Plainview, N.Y.

Sandig, V., R. Youil, et al. (2000). "Optimization of the helper-dependent adenovirus system for production and potency in vivo." *Proc Natl Acad Sci U S A* 97(3): 1002-7.

Schiedner, G., S. Hertel, et al. (2000). "Efficient transformation of primary human amniocytes by E1 functions of Ad5: generation of new cell lines for adenoviral vector production." *Human Gene Therapy* 11(15): 2105-16.

Schiedner, G., N. Morral, et al. (1998). "Genomic DNA transfer with a high-capacity adenovirus vector results in improved in vivo gene expression and decreased toxicity." *Nature Genetics* 18(2): 180-3.

Schmid, S. and P. Hearing (1997). "Bipartite structure and functional independence of adenovirus type 5 packaging elements." *J Virol* 71(5): 3375-3384.

Schmid, S. and P. Hearing (1998). "Cellular Components Interact with Adenovirus Type 5 Minimal DNA Packaging Domains." *J Gen Virol* 72(8): 6339-6347.

Schmitz, A., C. Coulondre, et al. (1978). "Genetic studies of the lac repressor. V. Repressors which bind operator more tightly generated by suppression and reversion of nonsense mutations." *J Mol Biol* 123(3): 431-54.

Silverstone, A. E., B. Magasanik et al. (1969). "Catabolite sensitive site of the lac operon." *Nature* 221(185):1012-4.

Stow, N. D. (1981). "Cloning a DNA fragment from the left-hand terminus of the adenovirus type 2 genome and its use in site-directed mutagenesis." *J Virol* 37: 171-180.

Ward G. A., C. K. Stover, et al. (1995). "Stringent chemical and thermal regulation of recombinant gene expression by vaccinia virus vectors in mammalian cells." *Proc Natl Acad Sci U S A* 92(15):6773-7.

Wold, William S. (1999) "Adenovirus Methods and Protocols", in *Methods in Molecular Medicine*, vol. 21, Humana Press, Totowa, N.J.

Worgall, S., P. L. Leopold, et al. (1997). "Role of alveolar macrophages in rapid elimination of adenovirus vectors administered to the epithelial surface of the respiratory tract." *Human Gene Therapy* 8(14): 1675-84.

Worgall, S., R. Singh, et al. (1999). "Selective expansion of alveolar macrophages in vivo by adenovirus-mediated transfer of the murine granulocyte-macrophage colony-stimulating factor cDNA." *Blood* 93(2): 655-66.

TABLE 1

| AV-VII(lac)[2] | | % Packaging Efficiency |
|---|---|---|
| +Ad-CMV | Experiment 1 | 4.8 |
| | Experiment 2 | 2.0 |
| | Experiment 3 | 8.8 |
| +Ad-lacWT | Experiment 1 | N.D. |
| | Experiment 2 | N.D. |
| | Experiment 3 | 0.85 |
| +Ad-lacX86 | Experiment 1 | 1.5 |
| | Experiment 2 | N.D. |
| | Experiment 3 | 0.55 |
| Ad-WT300 | | |
| +Ad-CMV | Experiment 1 | 31 |
| | Experiment 2 | 74 |
| +Ad-lacWT | Experiment 1 | 52 |
| | Experiment 2 | 33 |
| | Experiment 3 | 74 |
| +Ad-lacX86 | Experiment 1 | 45 |

TABLE 2

| Lacsite3/in340 | | % Packaging Efficiency |
|---|---|---|
| +Ad-CMV | Experiment 1 | 35 |
| | Experiment 2 | 21 |
| | Experiment 3 | 24 |
| | Experiment 4 | 28 |
| +Ad-lacWT | Experiment 1 | 13 |
| | Experiment 2 | 15 |
| | Experiment 3 | 11 |
| | Experiment 4 | 29 |

TABLE 3

| AV-VII(lac)[2] | | % Packaging Efficiency |
|---|---|---|
| Experiment 1 | +Ad-lacWT +IPTG | 23 |
| | +Ad-lacWT −IPTG | N.D. |
| | +Ad-CMV +IPTG | 13 |
| | +Ad-CMV −IPTG | 12 |
| Experiment 2 | +Ad-lacWT +IPTG | 11 |
| | +Ad-lacWT −IPTG | N.D. |
| | +Ad-CMV +IPTG | 12 |
| | +Ad-CMV −IPTG | 5 |
| Experiment 3 | +Ad-lacWT +IPTG | 5.9 |
| | +Ad-lacWT −IPTG | N.D. |
| | +Ad-CMV +IPTG | 16 |
| | +Ad-CMV −IPTG | 9.6 |

What is claimed is:

1. A recombinant helper Adenovirus (Ad) comprising an Ad helper genome nucleic acid sequence that comprises a) Ad sequences that encode structural and viral replication proteins required for growth and assembly of a gutted Ad, b) a binding site for a Lac repressor, wherein the binding site is located within the packaging domain of the recombinant helper Ad nucleic acid sequence, and c) a coding sequence for the Lac repressor wherein the coding sequence is (i) operatively linked to a promoter, and (ii) located within or in place of one of an E1A and an E1B gene of said helper adenovirus.

2. The recombinant helper Ad of claim 1 wherein the binding site for the Lac repressor is located in the cis-acting A repeats in the packaging domain of the recombinant helper Ad nucleic acid sequence.

3. The recombinant helper Ad of claim 1 wherein the recombinant Ad nucleic acid sequence comprises two binding sites for the Lac repressor located within the packaging domain.

4. The recombinant helper Ad of claim 1 wherein the Lac repressor is a temperature sensitive mutant.

5. The recombinant helper of claim 1 wherein the promoter is at least one of a CMV, a SV40, or a RSV promoter.

6. The recombinant helper Ad of claim 5 wherein the promoter is a CMV promoter.

7. A producer cell comprising the recombinant helper Ad of claim 1.

8. The producer cell of claim 7 wherein the cell is selected from the group consisting of 911, A549-E1, N52.E6, or KB-E1 cells.

9. A lysate stock comprising the recombinant helper Ad of claim 1.

10. A method for producing a gutted Ad substantially free of contaminating helper Ad, said method comprising (a) cotransfecting a producer cell with (i) a gutted Ad vector encoding the gutted Ad, and (ii) the recombinant helper Ad of claim 1; (b) growing the producer cell for a suitable time under conditions favorable for growth and packaging of the gutted Ad; and (c) wherein packaging of the recombinant helper Ad is suppressed by expression of the Lac repressor in the producer cell.

11. A recombinant helper Ad comprising an Ad helper genome nucleic acid sequence that comprises a) Ad sequences that encode structural and viral replication proteins required for growth and assembly of a gutted Ad, further comprising an E3 or an E4 region, b) a binding site for a Lac repressor, wherein the binding site is located within the packaging domain of the recombinant helper Ad nucleic acid sequence, and c) a coding sequence for the Lac repressor wherein the coding sequence is (i) operatively linked to a promoter, and (ii) located within or in place of the E3 or the E4 region.

12. The recombinant helper Ad of claim 11 wherein the binding site for the Lac repressor is located in the cis-acting A repeats in the packaging domain of the recombinant helper Ad nucleic acid sequence.

13. The recombinant helper Ad of claim 11 wherein the recombinant Ad nucleic acid sequence comprises two binding sites for the Lac repressor located within the packaging domain.

14. The recombinant helper Ad of claim 11 wherein the Lac repressor is a temperature sensitive mutant.

15. The recombinant helper of claim 11 wherein the promoter is at least one of a CMV, a SV40, or a RSV promoter.

16. The recombinant helper Ad of claim 15 wherein the promoter is a CMV promoter.

17. A producer cell comprising the recombinant helper Ad of claim 11.

18. The producer cell of claim 17 wherein the cell is selected from the group consisting of 911, A549-E1, N52.E6, or KB-E1 cells.

19. A lysate stock comprising the recombinant helper Ad of claim 11.

20. A method for producing a gutted Ad substantially free of contaminating helper Ad, said method comprising (a) cotransfecting a producer cell with (i) a gutted Ad vector, and (ii) the recombinant helper Ad of claim 11; (b) growing the producer cell for a suitable time under conditions favorable for growth and packaging of the gutted Ad; and (c) wherein packaging of the recombinant helper Ad is suppressed by expression of the Lac repressor in the producer cell.

21. A recombinant helper Ad comprising an Ad helper genome a nucleic acid sequence that comprises a) Ad sequences that encode structural and viral replication proteins, required for growth and assembly of a gutted Ad, b) a binding site for a Lac repressor, wherein the binding site is located within the packaging domain of the recombinant helper Ad nucleic acid sequence, and c) a coding sequence for the Lac repressor wherein the coding sequence is (i) operatively linked to a promoter, and (ii) located within or in place of both of an E1A and an E1B gene of said helper adenovirus.

* * * * *

UNITED STATES PATENT AND TRADEMARK OFFICE
CERTIFICATE OF CORRECTION

| | |
|---|---|
| PATENT NO. | : 7,585,498 B2 |
| APPLICATION NO. | : 10/490551 |
| DATED | : September 8, 2009 |
| INVENTOR(S) | : Hearing et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 510 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 7

<210> SEQ ID NO 1
<211> LENGTH: 14
<212> TYPE: DNA
<213> ORGANISM: Adenovirus
<220> FEATURE:
<221> NAME/KEY: misc_feature
<222> LOCATION: (5)..(12)
<223> OTHER INFORMATION: n is a, c, g, or t

<400> SEQUENCE: 1
tttgnnnnnn nncg                                                     14

<210> SEQ ID NO 2
<211> LENGTH: 118
<212> TYPE: DNA
<213> ORGANISM: Adenovirus
```

-continued

```
<400> SEQUENCE: 2
tcgaccgcgt aatatttgtc tagggccgcg gggactttga ccgtttacgt ggagactcct        60
cgaggagtct ccacgtaaac ggtcaaagtc cccgcggccc tagacaaata ttacgcgg        118

<210> SEQ ID NO 3
<211> LENGTH: 128
<212> TYPE: DNA
<213> ORGANISM: Adenovirus

<400> SEQUENCE: 3
tcgacaattg tgagcgctca caatttgtct agggccgcgg ggactttgac cgtttacgtg        60
gaggtcgacc tccacgtaaa cggtcaaagt ccccgcggcc ctagacaaat tgtgagcgct       120
cacaattg                                                               128

<210> SEQ ID NO 4
<211> LENGTH: 51
<212> TYPE: DNA
<213> ORGANISM: Adenovirus

<400> SEQUENCE: 4
tcgacaattg tgagcgctca caattcgtaa cactcgcgag tgttaagagc t               51

<210> SEQ ID NO 5
<211> LENGTH: 21
<212> TYPE: DNA
<213> ORGANISM: Escherichia coli

<400> SEQUENCE: 5
aattgtgagc ggataacaat t                                                 21

<210> SEQ ID NO 6
<211> LENGTH: 59
<212> TYPE: DNA
<213> ORGANISM: Adenovirus

<400> SEQUENCE: 6
tcgaccgcgt aatatttgtc tagggccgcg gggactttga ccgtttacgt ggagactcc        59

<210> SEQ ID NO 7
<211> LENGTH: 64
<212> TYPE: DNA
<213> ORGANISM: Artificial Sequence
<220> FEATURE:
<223> OTHER INFORMATION: Synthetic

<400> SEQUENCE: 7
tcgacaattg tgagcgctca caatttgtct agggccgcgg ggactttgac cgtttacgtg        60
gagg                                                                    64
```